(12) United States Patent
Teitelbaum et al.

(10) Patent No.: US 6,749,614 B2
(45) Date of Patent: Jun. 15, 2004

(54) FORMABLE ORTHOPEDIC FIXATION SYSTEM WITH CROSS LINKING

(75) Inventors: George P. Teitelbaum, Santa Monica, CA (US); Samuel M. Shaolian, Newport Beach, CA (US); To V. Pham, Trabuco Canyon, CA (US); Thanh Van Nguyen, Irvine, CA (US)

(73) Assignee: Vertelink Corporation, Irvine, CA (US)

( * ) Notice: Subject to any disclaimer, the term of this patent is extended or adjusted under 35 U.S.C. 154(b) by 150 days.

(21) Appl. No.: 09/976,459

(22) Filed: Oct. 10, 2001

(65) Prior Publication Data
US 2002/0068975 A1 Jun. 6, 2002

Related U.S. Application Data

(63) Continuation-in-part of application No. 09/943,636, filed on Aug. 29, 2001, which is a continuation-in-part of application No. 09/747,066, filed on Dec. 21, 2000.
(60) Provisional application No. 60/213,385, filed on Jun. 23, 2000.

(51) Int. Cl.$^7$ ................................................ A61B 17/56
(52) U.S. Cl. ........................................................ 606/61
(58) Field of Search ............................. 606/60, 61, 76; 623/17.12, 17.11

(56) References Cited

U.S. PATENT DOCUMENTS

| 2,267,925 A | 12/1941 | Johnston |
| 3,834,394 A | 9/1974 | Hunter et al. |

(List continued on next page.)

FOREIGN PATENT DOCUMENTS

| DE | 197 26 754 A1 | 2/1999 |
| RU | 839513 | 5/1981 |
| WO | WO 97/30666 | 8/1997 |
| WO | WO 97/38639 | 10/1997 |
| WO | WO 99/09902 | 3/1999 |
| WO | WO 99/15097 | 4/1999 |
| WO | WO 99/26549 | 6/1999 |
| WO | WO 00/44288 | 8/2000 |

OTHER PUBLICATIONS

Bennett, Gregory J., Lumbosacral Stabilization Using Screw Fixation Techniques, *Neurosurgery*, McGraw–Hill Health Professions Division, Second Edition, vol. II, pp. 3027–3035.

Kyphon Inc., *Kyphon: Fragility Fracture Management: About Kyphon*, 2000.

Müller, Adolf, M.D. et al. *A Keyhole Approach for Endoscopially Assisted Pedicle Screw Fixation in Lumbar Spine Instability, Neurosurgery*, vol. 47, No. 1, Jul. 2000, pp. 85–96.

Wilkins, Robert H., M.D. et al., *Neurosurgery*, 2$^{nd}$ Edition, vol. 1, pp. 3027–3035.

Adolf Muller et al., "A Keyhole Approach for endoscopially Assisted Pedicle Screw Fixation in Lumbar Spine Instability". Neurosuergery, vol. 47, No. 1, Jul. 2000, pp. 85–96.

Gregory J. Bennett, "Lumbosacral Stabilization Using Screw Fixation Techniques". Neurosuregery, 2$^{nd}$ Edition, vol. 2, pp. 3027–3035.

*Primary Examiner*—Eduardo C. Robert
(74) *Attorney, Agent, or Firm*—Knobbe, Martens, Olson & Bear, LLP.

(57) ABSTRACT

A subcutaneously assembled in place orthopedic construct is provided, such as for fixation of the spine. The construct includes a first bar and a second bar for attachment to the spine. A crossbar connects the first and second bar, to provide additional structural support. Each of the first bar, the second bar, and the crossbar may be inserted in a minimally invasive procedure, and constructed in place to form the orthopedic device. Each of the first bar, second bar, and crossbar may comprise an inflatable container, adapted for inflation with a hardenable media and cured in place. Methods and delivery structures are also disclosed.

33 Claims, 31 Drawing Sheets

U.S. PATENT DOCUMENTS

| | | | |
|---|---|---|---|
| 3,875,595 A | | 4/1975 | Froning |
| 4,041,939 A | | 8/1977 | Hall |
| 4,289,123 A | * | 9/1981 | Dunn .......................... 606/61 |
| 4,327,734 A | | 5/1982 | White, Jr. |
| 4,341,218 A | | 7/1982 | Ü |
| 4,364,392 A | | 12/1982 | Strother et al. |
| 4,383,879 A | | 5/1983 | Le Du et al. |
| 4,441,495 A | | 4/1984 | Hicswa |
| 4,517,979 A | | 5/1985 | Pecenka |
| 4,545,367 A | | 10/1985 | Tucci |
| 4,648,388 A | * | 3/1987 | Steffee .......................... 606/61 |
| 4,743,260 A | | 5/1988 | Burton |
| 4,772,287 A | | 9/1988 | Ray et al. |
| 4,887,595 A | * | 12/1989 | Heinig et al. ................. 606/61 |
| 4,904,260 A | | 2/1990 | Ray et al. |
| 4,998,936 A | * | 3/1991 | Mehdian ....................... 606/61 |
| 5,000,165 A | * | 3/1991 | Watanabe ..................... 606/61 |
| 5,030,220 A | * | 7/1991 | Howland ...................... 606/61 |
| 5,037,445 A | | 8/1991 | Sander et al. |
| 5,084,049 A | * | 1/1992 | Asher et al. .................. 606/61 |
| 5,108,404 A | | 4/1992 | Scholten et al. |
| 5,139,499 A | | 8/1992 | Small et al. |
| 5,146,933 A | | 9/1992 | Boyd |
| 5,165,919 A | | 11/1992 | Sasaki et al. |
| 5,171,279 A | | 12/1992 | Mathews |
| 5,171,280 A | | 12/1992 | Baumgartner |
| 5,176,680 A | | 1/1993 | Vignaud et al. |
| 5,181,921 A | | 1/1993 | Makita et al. |
| 5,222,970 A | | 6/1993 | Reeves |
| 5,242,443 A | | 9/1993 | Kambin |
| 5,242,444 A | | 9/1993 | MacMillan |
| 5,324,261 A | | 6/1994 | Amundson et al. |
| 5,342,361 A | | 8/1994 | Yaun et al. |
| 5,357,983 A | | 10/1994 | Mathews |
| 5,397,363 A | * | 3/1995 | Gelbard ........................ 606/61 |
| 5,470,336 A | | 11/1995 | Ling et al. |
| 5,474,551 A | * | 12/1995 | Finn et al. .................... 606/61 |
| 5,486,174 A | * | 1/1996 | Fournet-Fayard et al. .... 606/61 |
| 5,496,322 A | | 3/1996 | Mathews |
| 5,520,689 A | | 5/1996 | Schlapfer et al. |
| 5,529,653 A | | 6/1996 | Glastra |
| 5,549,679 A | | 8/1996 | Kuslich |
| 5,556,429 A | | 9/1996 | Felt |
| 5,562,661 A | * | 10/1996 | Yoshimi et al. ............... 606/61 |
| 5,562,736 A | | 10/1996 | Ray et al. |
| 5,569,248 A | | 10/1996 | Mathews |
| 5,571,189 A | | 11/1996 | Kuslich |
| 5,584,887 A | | 12/1996 | Kambin |
| 5,591,165 A | | 1/1997 | Jackson |
| 5,591,167 A | | 1/1997 | Laurain et al. |
| 5,591,199 A | | 1/1997 | Porter et al. |
| 5,593,408 A | | 1/1997 | Gayet et al. |
| 5,649,925 A | | 7/1997 | Alacreu |
| 5,658,286 A | | 8/1997 | Sava |
| 5,720,751 A | | 2/1998 | Jackson |
| 5,728,097 A | | 3/1998 | Mathews |
| 5,752,955 A | * | 5/1998 | Errico .......................... 606/61 |
| 5,772,661 A | | 6/1998 | Michelson |
| 5,779,672 A | | 7/1998 | Dormandy, Jr. |
| 5,792,044 A | | 8/1998 | Foley et al. |
| 5,795,353 A | | 8/1998 | Felt |
| 5,800,435 A | | 9/1998 | Errico et al. |
| 5,827,289 A | | 10/1998 | Reiley et al. |
| 5,888,220 A | | 3/1999 | Felt et al. |
| 5,899,939 A | | 5/1999 | Boyce et al. |
| 5,910,142 A | | 6/1999 | Tatar |
| 5,938,663 A | | 8/1999 | Petreto |
| 5,972,015 A | | 10/1999 | Scribner et al. |
| 5,980,253 A | | 11/1999 | Oxman et al. |
| 6,025,406 A | | 2/2000 | Oxman et al. |
| 6,033,406 A | | 3/2000 | Mathews |
| 6,042,380 A | | 3/2000 | De Rowe |
| 6,043,295 A | | 3/2000 | Oxman et al. |
| 6,048,346 A | | 4/2000 | Reiley et al. |
| 6,066,154 A | | 5/2000 | Reiley et al. |
| 6,080,801 A | | 6/2000 | Draenert et al. |
| 6,099,528 A | | 8/2000 | Saurat |
| 6,102,912 A | | 8/2000 | Cazin et al. |
| 6,106,530 A | | 8/2000 | Harada |
| 6,123,707 A | | 9/2000 | Wagner |
| 6,126,689 A | | 10/2000 | Brett |
| 6,127,597 A | | 10/2000 | Beyar et al. |
| 6,149,655 A | | 11/2000 | Constantz et al. |
| 6,159,012 A | | 12/2000 | Oxman et al. |
| 6,174,334 B1 | | 1/2001 | Suddaby |
| 6,175,758 B1 | | 1/2001 | Kambin |
| 6,176,882 B1 | | 1/2001 | Biedermann et al. |
| 6,206,922 B1 | * | 3/2001 | Zdeblick et al. ......... 623/17.11 |
| 6,226,548 B1 | | 5/2001 | Foley et al. |
| 6,235,028 B1 | | 5/2001 | Brumfield et al. |
| 6,241,734 B1 | | 6/2001 | Scribner et al. |
| 6,280,456 B1 | | 8/2001 | Scribner |
| 6,296,644 B1 | | 10/2001 | Saurat et al. |
| 6,306,177 B1 | | 10/2001 | Felt et al. |
| 6,332,894 B1 | | 12/2001 | Stalcup et al. |
| 6,395,034 B1 | | 5/2002 | Suddaby |
| 6,402,784 B1 | | 6/2002 | Wardlaw |
| 6,443,988 B2 | | 9/2002 | Felt et al. |
| 6,447,514 B1 | | 9/2002 | Stalcup |
| 6,530,926 B1 | | 3/2003 | Davison |
| 6,530,929 B1 | | 3/2003 | Justis et al. |
| 6,558,386 B1 | | 5/2003 | Cragg |
| 6,558,390 B2 | | 5/2003 | Craig |
| 2001/0004710 A1 | | 6/2001 | Felt et al. |
| 2002/0022764 A1 | | 2/2002 | Smith et al. |
| 2002/0045904 A1 | | 4/2002 | Fuss et al. |
| 2002/0068975 A1 | | 6/2002 | Teitelbaum et al. |
| 2002/0082598 A1 | | 6/2002 | Teitelbaum |
| 2002/0082600 A1 | | 6/2002 | Shaolian et al. |
| 2002/0082601 A1 | | 6/2002 | Toyama et al. |
| 2002/0161368 A1 | | 10/2002 | Foley et al. |
| 2002/0198526 A1 | * | 12/2002 | Shaolian et al. ............... 606/61 |
| 2003/0028251 A1 | | 2/2003 | Mathews |
| 2003/0060826 A1 | | 3/2003 | Foley et al. |
| 2004/0006341 A1 | * | 1/2004 | Shaolian et al. ............... 606/61 |

* cited by examiner

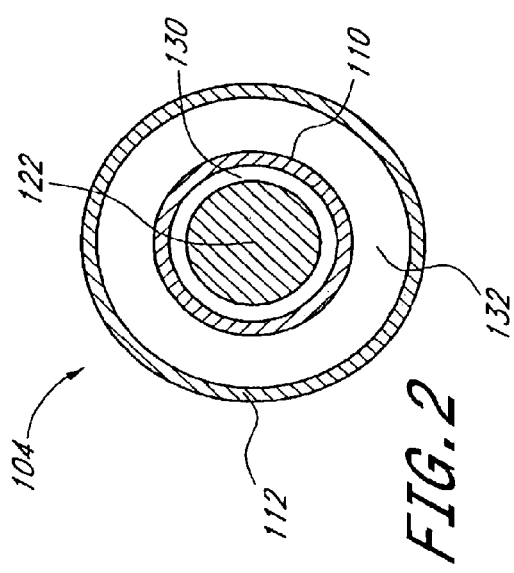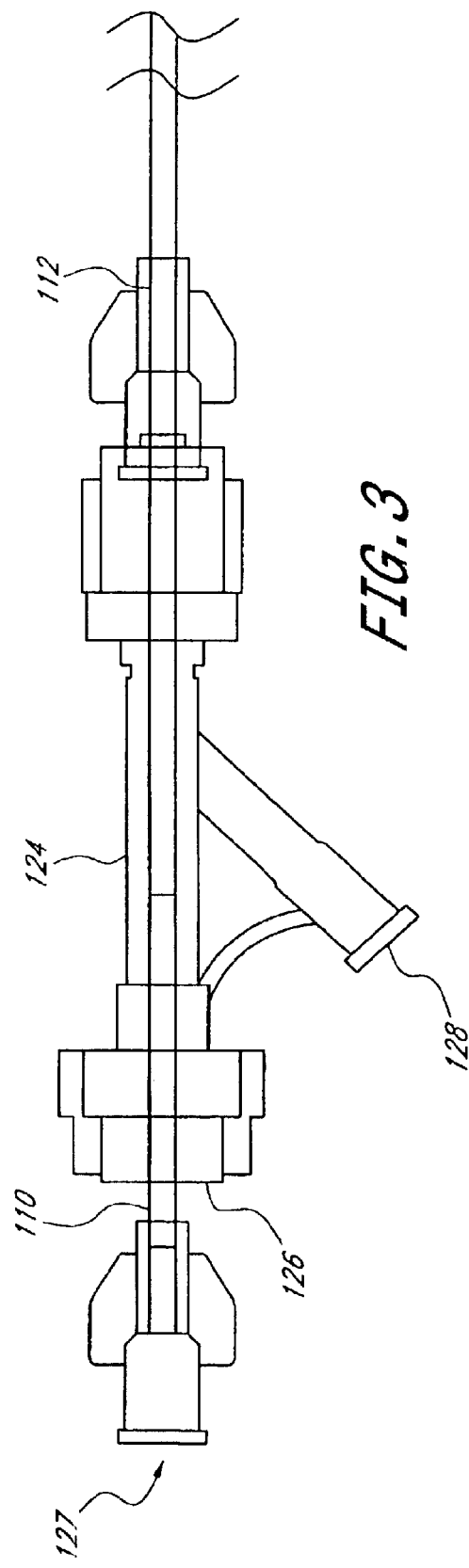

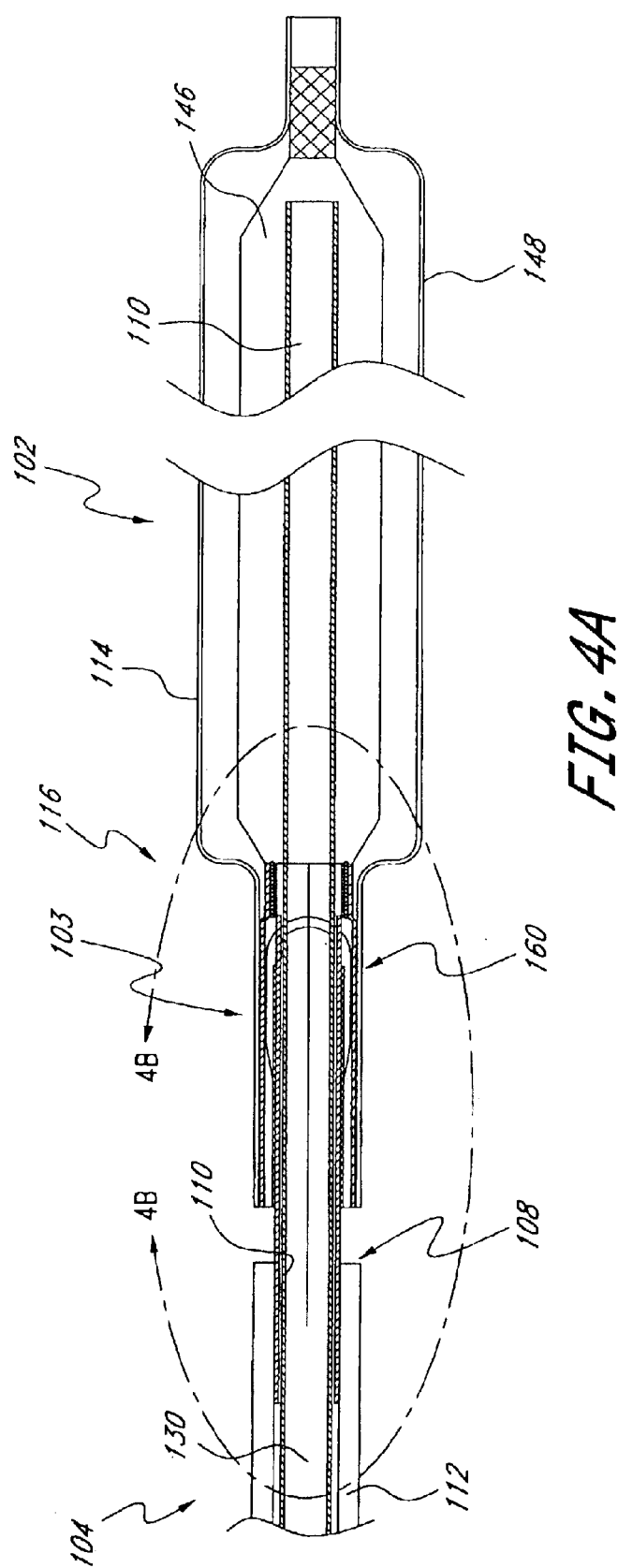

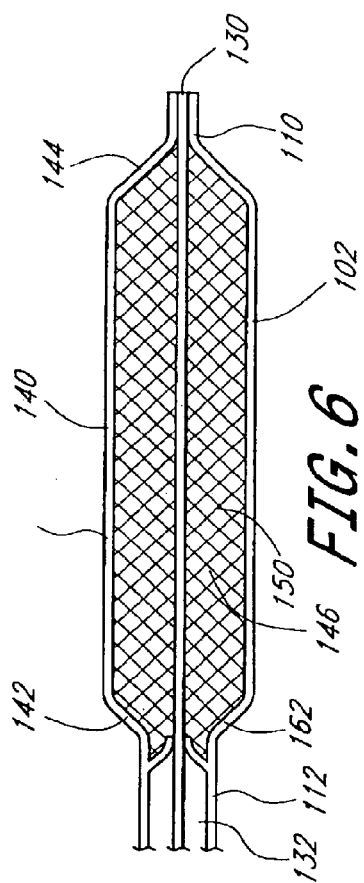
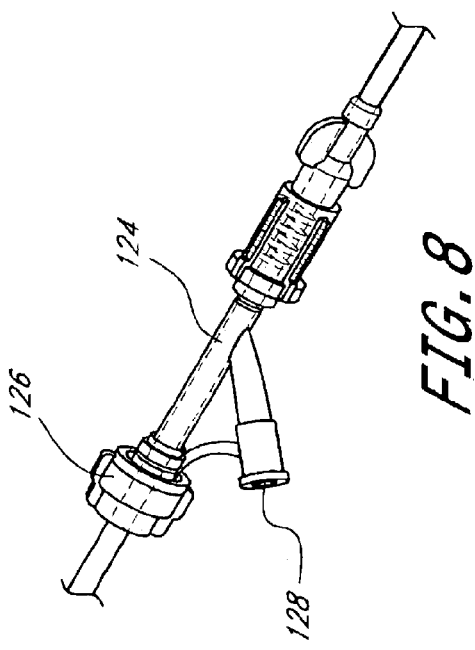
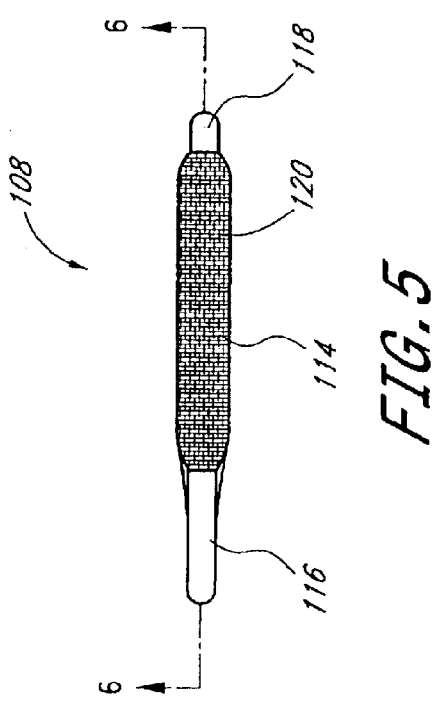
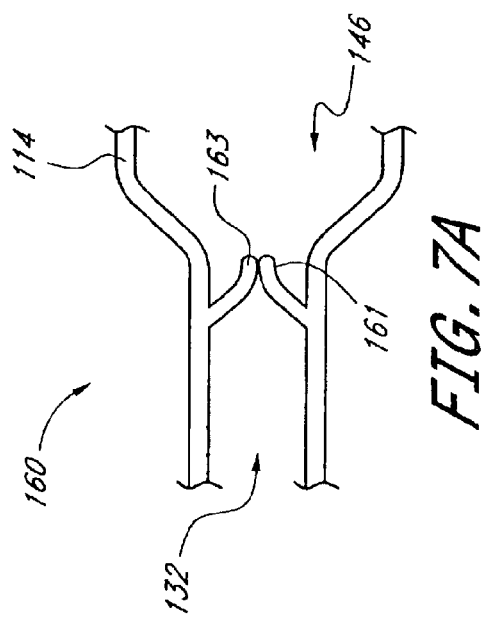

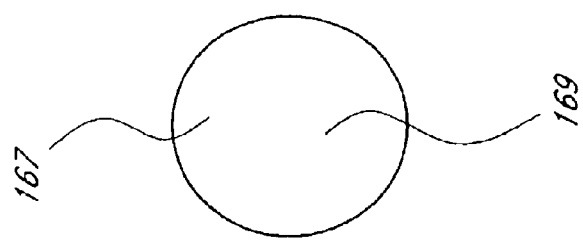
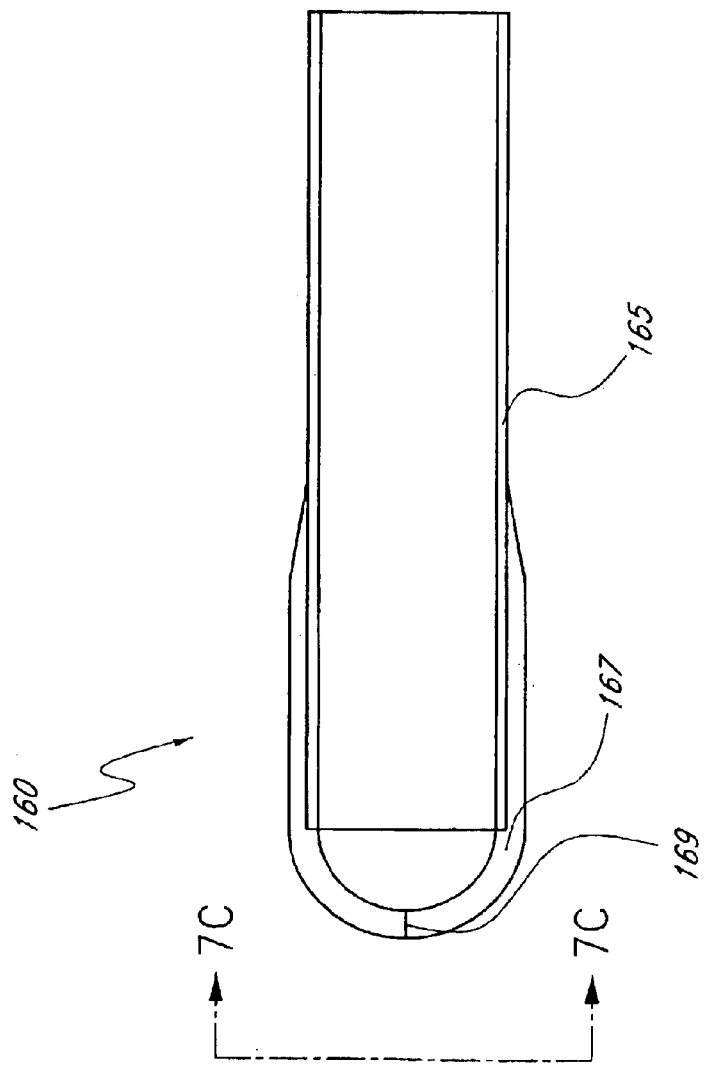

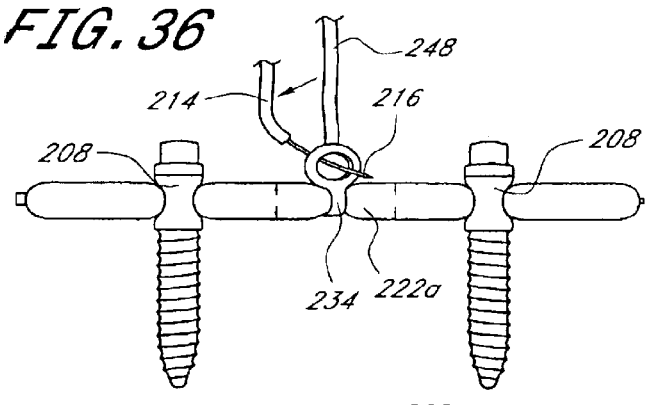
FIG. 36
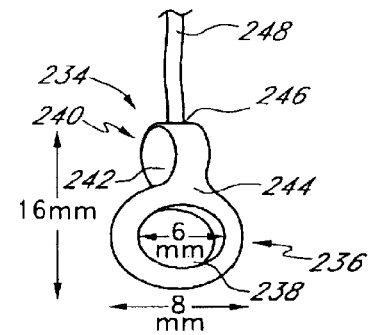
FIG. 37
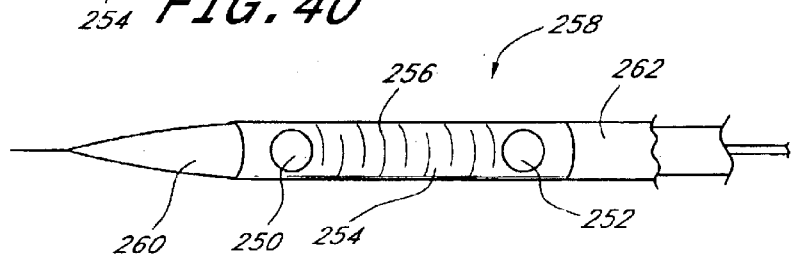
FIG. 40
FIG. 41
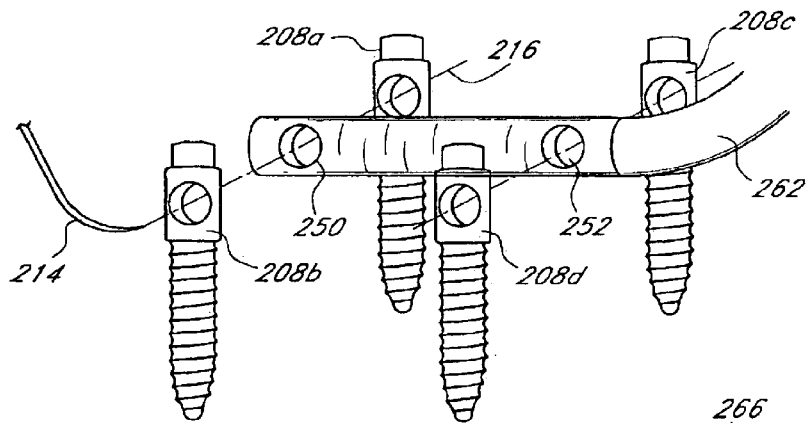
FIG. 42
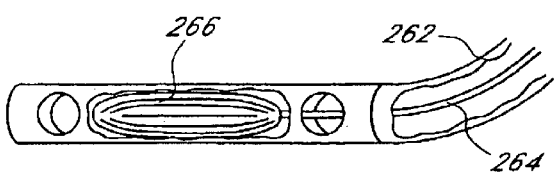
FIG. 43

FORMABLE ORTHOPEDIC FIXATION SYSTEM WITH CROSS LINKING

This is a continuation-in-part of U.S. patent application Ser. No. 09/943,636, filed on Aug. 29, 2001, which is a continuation-in-part of U.S. patent application Ser. No. 09/747,066, filed on Dec. 21, 2000, which claims priority to U.S. Provisional Patent Application 60/213,385, filed Jun. 23, 2000, entitled "Percutaneous Interbody Fusion Device," the contents of each of which are incorporated in their entirety into this disclosure by reference.

BACKGROUND OF THE INVENTION

1. Field of the Invention

The present invention relates to medical devices and, more particularly, to systems for forming orthopedic fixation or stabilization implants in place within the body, such as by infusing a formable media into a cavity. In one application, the present invention relates to minimally invasive procedures and devices for forming a spinal stabilization rod in situ.

2. Description of the Related Art

The human vertebrae and associated connective elements are subject to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to these diseases, conditions, injuries and manipulations often result from the displacement of all or part of a vertebra from the remainder of the vertebral column. A variety of methods have been developed to restore the displaced vertebrae or portions of displaced vertebrae to their normal position and to fix them within the vertebral column. For example, open reduction with screw fixation is one currently used method. The surgical procedure of attaching two or more parts of a bone with pins, screws, rods and plates requires an incision into the tissue surrounding the bone and the drilling of one or more holes through the bone parts to be joined. Due to the significant variation in bone size, configuration, and load requirements, a wide variety of bone fixation devices have been developed in the prior art. In general, the current standard of care relies upon a variety of metal wires, screws, rods, plates and clamps to stabilize the bone fragments during the healing or fusing process. These methods, however, are associated with a variety of disadvantages, such as morbidity, high costs, lengthy in-patient hospital stays and the pain associated with open procedures.

Therefore, devices and methods are needed for repositioning and fixing displaced vertebrae or portions of displaced vertebrae which cause less pain and potential complications. Preferably, the devices are implantable through a minimally invasive procedure.

SUMMARY OF THE INVENTION

There is provided in accordance with one aspect of the present invention, a method of treating the spine. The method comprises the steps of attaching a first support structure to the spine, and attaching a second support structure to the spine. A crossbar is attached to the first and second support structures, and at least the attaching a crossbar step comprises advancing at least a portion of the crossbar between the spine and a muscle layer.

In accordance with another aspect of the present invention, there is provided a method of treating a patient. The method comprises the steps of securing a first rod at a first site in the patient. A second rod is secured at a second site in the patient. Curable media is introduced in between the first and second rods to form a cross link. The first rod is linked to the second rod by permitting the media to cure.

The introducing step in one application of the invention comprises introducing the curable media into a tubular media support structure extending between the first and second rods. The support structure may comprise a balloon. Preferably, the method is accomplished percutaneously.

There is provided in accordance with a further aspect of the present invention, a subcutaneously assembled in place orthopedic construct. The construct comprises a first support structure, attached to the spine. A second support structure is also attached to the spine. A crossbar connects the first support structure to the second support structure to form an orthopedic construct. The crossbar is attached to the first and second support structures subcutaneously, without the need for an open surgical cutdown.

The first support structure preferably comprises a hardenable media, and the second support structure preferably also comprises a hardenable media. The crossbar may additionally comprise a hardenable media. A first cross tie may be provided, to connect the crossbar to the first support, and a second cross tie may be provided to connect the crossbar to the second support. Alternatively, the crossbar includes a first aperture for receiving the first support and a second aperture for receiving the second support.

At least the first support structure and, in some applications both the first and the second support structure comprises an outer wall, defining a cavity therein. A plurality of reinforcing fibers are positioned in the cavity, and a hardenable media for bonding with the reinforcing fibers is provided in the cavity to form the support structure. The hardenable media may be hardened while the support structure is positioned within the body of a patient, to create an orthopedic construct.

The hardenable media comprises an epoxy, a polyurethane, or other curable material. The reinforcing fibers may comprise carbon fibers, stainless steel or other reinforcing fibers.

In one application, the reinforcing fibers comprise graphite fibers having a diameter within the range of from about 0.003 inches to about 0.007 inches. The reinforcing fibers may be provided in at least one bundle, having within the range of from about 3,000 to about 12,000 fibers.

The reinforcing fibers may have a tow tensile strength within the range of from about 5,000 MPA to about 7,000 MPA. The reinforcing fibers may have a tow tensile modulus within the range of from about 250 GPA to about 350 GPA. Preferably, at least one reinforcing sleeve is provided within the cavity.

Further features and advantages of the present invention will become apparent to those of skill in the art in view of the detailed description of preferred embodiments which follows, when considered together with the attached claims and drawings.

BRIEF DESCRIPTION OF THE DRAWING

FIG. 2 is a cross-sectional view taken along the line 2—2 of the delivery catheter of FIG. 1.

FIG. 3 is a side elevational cross section of a proximal portion of the delivery catheter of FIG. 1.

FIG. 4A is a side elevational cross section of a distal portion of the delivery catheter of FIG. 1.

FIG. 5 is a side elevational view of the inflatable fixation device of FIG. 1.

FIG. 6 is a cross-sectional view through the inflatable fixation device of FIG. 5, in the expanded position.

FIG. 7A is a schematic cross-sectional view of a valve of the inflatable fixation device of FIG. 6.

FIG. 7B is a schematic cross-sectional view of an alternate valve.

FIG. 7C is an end view of the valve of FIG. 7B.

FIG. 8 is a perspective view of the manifold of the delivery catheter of FIG. 1

FIG. 36 is a perspective, schematic view of various components of the cross tie system.

FIG. 37 is a perspective view of a cross tie.

FIG. 40 is a side elevational perspective view of a tubular crossbar sheath.

FIG. 41 is a side elevational schematic view of the crossbar sheath of FIG. 40, mounted on a deployment catheter.

FIG. 42 is a schematic perspective view of the crossbar deployment system of FIG. 41, positioned within two pairs of opposing pedicle screws.

FIG. 43 is a partial cutaway side elevational view of a sheath as in FIG. 40, having an inflatable balloon positioned therein.

DETAILED DESCRIPTION OF THE PREFERRED EMBODIMENT

Although the application of the present invention will be disclosed primarily in connection with a spinal fixation procedure, the methods and devices disclosed herein are intended for use in any of a wide variety of medical applications where formation of an attachment, bulking, support, fixation or other element in situ may be desirable.

One advantage of the in situ prosthesis formation in accordance with the present invention is the ability to obtain access to a treatment site through a minimally invasive access pathway, while enabling the formation of a relatively larger implant at the treatment site. This allows procedure morbidity to be minimized, since open surgical cutdowns or other invasive access procedures may be avoided. In addition, the in situ formation in accordance with the present invention allows the formation of an implant having any of a wide variety of customized or predetermined shapes, due to the ability of the infusible hardenable media to assume the shape of the cavity or flexible container into which it is infused.

The methods and devices of the present invention additionally enable access to a treatment site within the body along a curved and even tortuous pathway, through which a preformed prosthesis would not fit or would not be navigable. The detachable inflatable prosthesis of the present invention, removably coupled to the distal end of an elongate flexible tubular catheter body, can be dimensioned for percutaneous, surgical or transluminal advancement and deployment of an inflatable or otherwise curable in place prosthesis in any of a wide variety of orthopedic applications, such as the spine as disclosed in greater detail below, as well as long bones, short bones, and associated ligaments and tendons. In addition, the deployment catheter and prosthesis can be dimensioned for transluminal navigation throughout the cardiovascular system, the gastrointestinal tract, the biliary tract, the genitourinary tract, or the respiratory tract (e.g. the tracheobronchial tree). The device may thus be advanced through artificial access pathways as well as naturally occurring lumens and hollow organs. Additional applications of the in situ device formation technology of the present invention will become apparent to those of skill in the art in view of the disclosure herein.

In connection with spinal fixation applications, the present invention involves inserting one or two or more bone anchors having a connector such as a portal into at least a first and a second adjacent or nonadjacent vertebra. An implantable, inflatable orthopedic device is inserted through the portals and inflated to lock to the bone anchors and stabilize the bone components. A deployment system, comprising a delivery catheter removably carrying the implantable device, is provided, such that the procedure may be conducted in a percutaneous or minimally invasive manner to minimize procedure trauma to the patient.

Figure 1:
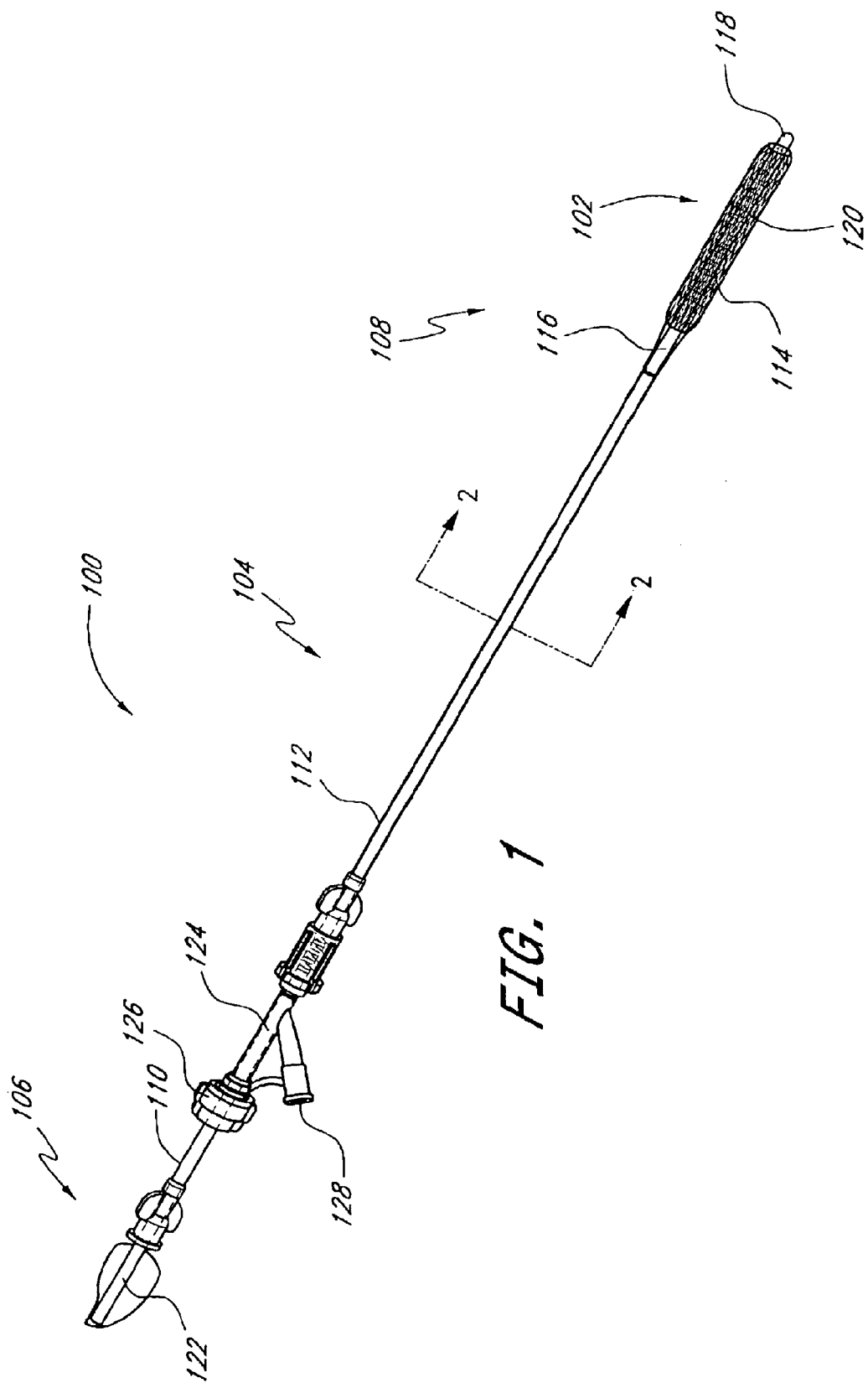
FIG. 1 is a side elevational view of a delivery catheter having an inflatable fixation device thereon.

The deployment system shown in FIG. 1 comprises a delivery catheter 100 which deploys the implantable inflatable orthopedic device 102. Delivery catheter 100 preferably includes an elongate, flexible tubular body 104, having a proximal end 106 and a distal end 108. For certain applications, however, in which direct linear access is intended, the tubular body 104 may be substantially rigid. The tubular body 104 includes one or more passages or lumens extending axially through the body, depending upon the desired functionality of the device.

The overall length and cross sectional dimensions of the delivery catheter 100 may be varied, depending upon the intended clinical application. In a device intended for percutaneous or minimally invasive fusion of lumbar and/or sacral vertebrae, for example, the tubular body 104 will generally have a length within the range of from about 15 cm to about 30 cm, and a diameter within the range of from about 2 mm to about 3 mm.

Percutaneous insertion of the delivery catheter 100 may be facilitated by the provision of a removable elongate stiffening wire 122, extending through a lumen such as inflation lumen 130 (see FIG. 2) from the proximal end 106 of tubular body 104, to the distal end 108 of tubular body 104. Optionally, the stiffening wire 122 extends into, and even all the way to the distal end 118 of the orthopedic device 102, to provide support and column strength to the device 102 which may be desirable during tissue penetration.

FIG. 2 shows a cross-sectional view through the elongate body 104, showing (not to scale) an inner sleeve 110 and an outer sleeve 112. The inner sleeve 110 defines a first, inflation lumen 130, while a second, venting lumen 132 is defined by the annular space between the inner sleeve 110 and outer sleeve 112. The inflation lumen 130 is adapted to receive the elongate stiffening wire 122 in a sliding fashion through a proximal opening 127 on inner sleeve 110, which in turn extends axially into the outer sleeve 112 by way of port 126 in catheter manifold 124. Although the illustrated embodiment has a dual lumen, concentric or coaxial configuration, three or more lumen may alternatively be provided, depending upon the desired capabilities of the catheter. A single lumen catheter may also be provided, to accommodate a removable stiffening wire, if utilized, and to facilitate inflation of the implantable device. Alternatively, a two or more lumen catheter shaft may be fabricated, extruded or otherwise formed with the lumen in a side-by-side configuration.

The deployment device 100 further comprises a manifold 124, located at the proximal end 106 of the elongate tubular body 104. The catheter manifold 124 provides a maneuvering handle for the health care professional, and supports an inflation port 126 and a vent port 128. Either or both the inflation port 126 or the vent port 128 may be provided with a coupling, such as a luer-lock fitting for connection to associated devices as is known in the art. For example, a luer or other connector on the inflation port 126 facilitates connection to a source of pressurized inflation media in a conventional manner. The vent port 128 may be connected to a syringe or other device to draw a vacuum, to evacuate air from the balloon prior to infusion of the hardenable media.

The manifold 124 may also include an injection port for allowing injection of radiopaque contrast fluid to enable visualization of the delivery device on a fluoroscope. The proximal manifold 124 may be machined or injection molded of any of a variety of known suitable materials such as PTFE, nylon, polyethylene, or others known in the art. A precision gasket may also be provided, which seals securely around the inner sleeve 110, prohibiting fluid loss.

Catheter manufacturing techniques are generally known in the art, including extrusion and coextrusion, coating, adhesives, and molding. The catheter of the present invention is preferably made in a conventional manner. The elongate shaft of the catheter may be extruded, using polymers such as Nylon, PEBAX, PEEK, PTFE, PE or others known in the catheter arts, the stiffness of which may be selected as appropriate. Material selection varies based on the desired characteristics. The joints are preferably bonded. Biocompatible adhesives or heat bonding may be used to bond the joints. The balloon and stent are also made in a conventional manner.

The deployment system 100 further comprises an implantable inflatable orthopedic device 102, which may function, in a spinal fusion application, as an inflatable or formed in place fixation plate or rod. Implantable device 102 is removably carried by the distal end of the tubular body 104, such that inflation lumen 130 is in communication with the interior cavity 146 of the inflatable device 102. The inflation media may thus be infused through inflation port 126 (or opening 127) located at manifold 124 to fill the cavity 146.

The implantable device 102, which may be a balloon 114, includes a proximal end 116, a distal end 118, and a flexible wall 148. The balloon 114 may be formed from any of a variety of polymeric materials which are known in the balloon angioplasty arts. These include, for example, complaint materials such as polyethylene, polyethylene blends or nylon, and substantially noncompliant materials such as polyethylene terephthalate. Any of a wide variety of other biocompatible polymers may be utilized, as will be apparent to those of skill in the art in view of the disclosure herein.

The balloon 114 may comprise a single or multiple layers, depending upon the desired physical properties. In one embodiment, the balloon comprises two layers, having a reinforcing structure such as a stent or a plurality of axially extending support strips sandwiched therebetween. In an alternate embodiment, the balloon 114 comprises a first, inner layer which restrains the hardenable media. A second, outer layer is coaxially disposed about the first layer, and is provided with a plurality of apertures or a microporous structure. An infusion lumen is provided in the elongate tubular body, for providing communication between a proximal infusion port and the space in between the inner and outer balloon layers. In this manner, fluids, which may contain any of a variety of medications, can be infused into the tissue surrounding the treatment site. Suitable structures and manufacturing considerations are disclosed in U.S. Pat. No. 5,295,962 to Crocker et al., the disclosure of which is incorporated in its entirety herein by reference.

Although a cylindrical configuration for balloon 114 is illustrated herein, any of a variety of alternative cross sectional configurations may be utilized. The overall length, diameter and wall thickness of the implantable inflatable orthopedic device 102 may be varied, depending on the particular treatment and access site. In one embodiment, device 102 has an inflated length between about 2 and 12 cm, and often between about 5 cm and about 8 cm for adjacent vertebrae fixation. The device 102 has an inflated diameter of generally between about 0.5 and 2 cm.

The length of the balloon 114 is based upon the anticipated distance between the first and second anchors, or, in an embodiment having more than two anchors, between the anchors having the greatest axial separation. For example, in a fusion application in which two adjacent lumbar vertebrae (e.g. L4–L5) are to be fused in an adult, the first and second anchors will generally be spaced apart by a distance within the range of from about 5 cm to about 8 cm. Preferably, the axial length of the balloon 114 is sufficiently longer than the inter anchor spacing to permit a portion of the balloon to expand on the "far" side of the anchor aperture as is illustrated, for example, in FIG. 9. Thus, balloon lengths for the above identified inter anchor distances will generally exceed the sum of the inter anchor distance and the anchor diameters by at least about 0.5 cm. Preferably, the balloon extends at least about 1 cm beyond the portals.

For use in an application where a first vertebrae is attached to a second vertebrae, and the second vertebrae is separated from the first vertebrae by at least a third vertebrae, for example in the lumbar spine, the inter anchor distance will generally be within the range of from about 10 cm to about 20 cm. As will be appreciated by those of skill in the art, in a three or more vertebrae fixation, the intermediate vertebrae or vertebraes will normally but need not necessarily be connected to the inflatable balloon 114. Thus, in one application, the balloon 114 connects a first attachment point at a first bone and a second attachment point at a second bone, with one or more intermediate bones unconnected to the balloon 114. In another application, at least a third anchor is provided in between the first and second anchors, and the balloon 114 is threaded through an aperture on each of the first, second and third anchors. The desirability of attaching or leaving unattached intervening vertebrae or other bones or structures between two attachment points is a matter of clinical judgement, in view of the particular circumstances of the patient.

The primary function of the balloon 114 is to influence or control the shape of the hardenable media, following injection therein. The implantable balloon 114 is not normally required to restrain pressure over an extended period of time. Thus, a greater design flexibility may be permitted, compared to conventional angioplasty or other dilatation balloons. For example, the balloon 114 may be porous, either for drug delivery as has been discussed, or to permit osteoincorporation and/or soft tissue ingrowth.

Certain hardenable media which may be utilized in connection with the present invention, such as PMMA, have a significantly greater viscosity in the precured form, compared to conventional angioplasty balloon inflation media. In addition, since the balloon 114 is not intended to contain significant pressure, conventional high strength materials such as for high pressure angioplasty may not be necessary. This allows the balloon 114 to be constructed in any of a variety of ways, including techniques utilized for balloon angioplasty applications. In addition, the balloon 114 (or balloon-like structure) may be made out of any of a wide variety of woven or nonwoven fibers, fabrics, metal mesh such as woven or braided wires, and carbon. Biocompatible fabrics or sheet material such as ePTFE and Dacron® may also be used.

The hardenable media is preferably a rapid setting, liquid polymer or polymer precursor, such as polymethyl methacrylate. However, any of a variety of other materials which provide the required stiffening or setting characteristics may be used, including any of a variety of epoxies, polyurethane or blends of polyurethane-silicone.

In the context of a rod shaped inflatable container, for use in spinal fixation procedures, the physical requirements of the hardenable media will depend upon the length and diameter of the rod as well as the physical requirements imposed by the implantation site. For certain embodiments, polymethyl methacrylate, epoxy, polyurethane or other particular material may or may not exhibit sufficient physical properties. Physical properties of hardenable materials can be modified through the addition of any of a variety of additives, such as carbon fibers, Kevlar or Titanium Rods, woven or laser etched metallic tubular stents, or other strength enhancers as will be understood in the art. The selection of a particular hardenable media, as well as the desirability of adding strength, flexibility, or other physical property enhancers, can be optimized for any particular implantation system through routine experimentation by those of skill in the art in view of the disclosure herein.

Certain composite materials, such as carbon fibers embedded in a bonding agent such as a two part epoxy, or two part polyurethane have been found particularly useful in forming the implant of the present invention. For example, graphite (carbon fibers) having a diameter within the range of from about 0.003 to about 0.007 inches are provided in bundles (tows) composed of from about 3,000 to about 12,000 fibers. One typical fiber useful for this purpose is manufactured by Hexcel Carbon Fibers, Salt Lake City, Utah, Part No. HS/CP-5000/IM7-GP 12K. Preferably, the Tow tensile strength is in the range of from about 5,000 to about 7,000 Mpa. Tow tensile modulus is within the range of from about 250 to about 350 Gpa.

In general, the composite rods in accordance with the present invention will exhibit a static compression bending values (per ASTM F1717) within the range of from about 100 to about 200 lbs., and, preferably greater than about 150 lbs. The composite rods will exhibit a static torsion (per ASTM F1717) within the range of from about 300 to about 500 inch pounds, and, generally in excess of about 400 inch pounds. The rods will preferably reach at least about 5 million cycles, at 5 Hz. Each of these parameters may be measured in accordance with the protocols described in the American Society for Testing and Materials (ASTM) designation F 1717-96, a copy of which is attached hereto as Appendix A, and which is incorporated in its entirety herein by reference.

Within the range of from about 30 to about 60 bundles of the carbon fiber described above is packed in a deflated balloon, along with a Ni—Ti stent having an 8 mm diameter and 8 cm length. Although any of a variety of stents may be utilized, one useful structure is similar to the Smart Stent (Cordis), and it helps keep the structure intact and also adds structural strength to the implanted structure.

A one or a two part epoxy having a viscosity in the range of from about 100 to about 500 cps is then injected into the balloon under pressure such as by using a pump and pressure within the range of from about 4 ATM to about 10 ATM or more depending upon viscosity, balloon strength and other design considerations. The pump is run for a sufficient duration and under a sufficient pressure to ensure that the epoxy wets all of the fibers. This may range from about 10 minutes or more to about an hour, and, in one application where the pump was run at about 5 ATM pressure, requires at least about ½ hour. Specific method parameters may be optimized depending upon the viscosity of the epoxy, infusion pressure, infusion flow rate, density of the packed carbon fibers, and other variables as will be apparent to those of skill in the art in view of the disclosure herein.

In an alternate embodiment, carbon fibers having within the range of from about 15 to about 45 degrees of braids are utilized. The braid may be in the form of a plain weave, and may be obtained, for example, from Composite Structures Technology (Tehachapi, Calif.). A 0.5 inch diameter of 45 degrees braided carbon fiber sleeve is positioned within the center of the balloon. This braided sleeve conforms dimensionally to the inside diameter of the balloon. A 0.3 inch diameter braided carbon sleeve (again 45°×45° plain weave) is positioned concentrically within the balloon, within the outer braided carbon fiber sleeve. Unidirectional fibers are thereafter introduced inside of the ID of the inner braided carbon sleeve. Unidirectional fibers are also introduced into the annular gap between the two braided sleeves. The volume of the fiber per volume of balloon is generally within the range of from about 40% to about 55%. After placement of the foregoing structure within the portals of the screws, the epoxy mix having a viscosity within the range of from about 500 to about 1000 cps is injected under 10 atmospheres pressure into the balloon.

Although the foregoing composite structure was described using a carbon fiber example, any of a variety of fibers may be positioned within the balloon to enhance the physical properties of the finished product. For example, Kevlar fibers, PEEK, and any of a variety of alternatives may be used. In general, the fibers will preferably provide a very high tensile strength and high modulus, having a low diameter to enhance deliverability of the device.

The use of braided sleeves will produce higher structural resistance to sheer stress as a result of torsional loads, plus the ability to distribute unidirectional fibers in a homogenous manner within the balloon at all times. This appears to improve the performance of the implant.

Figure 4B:
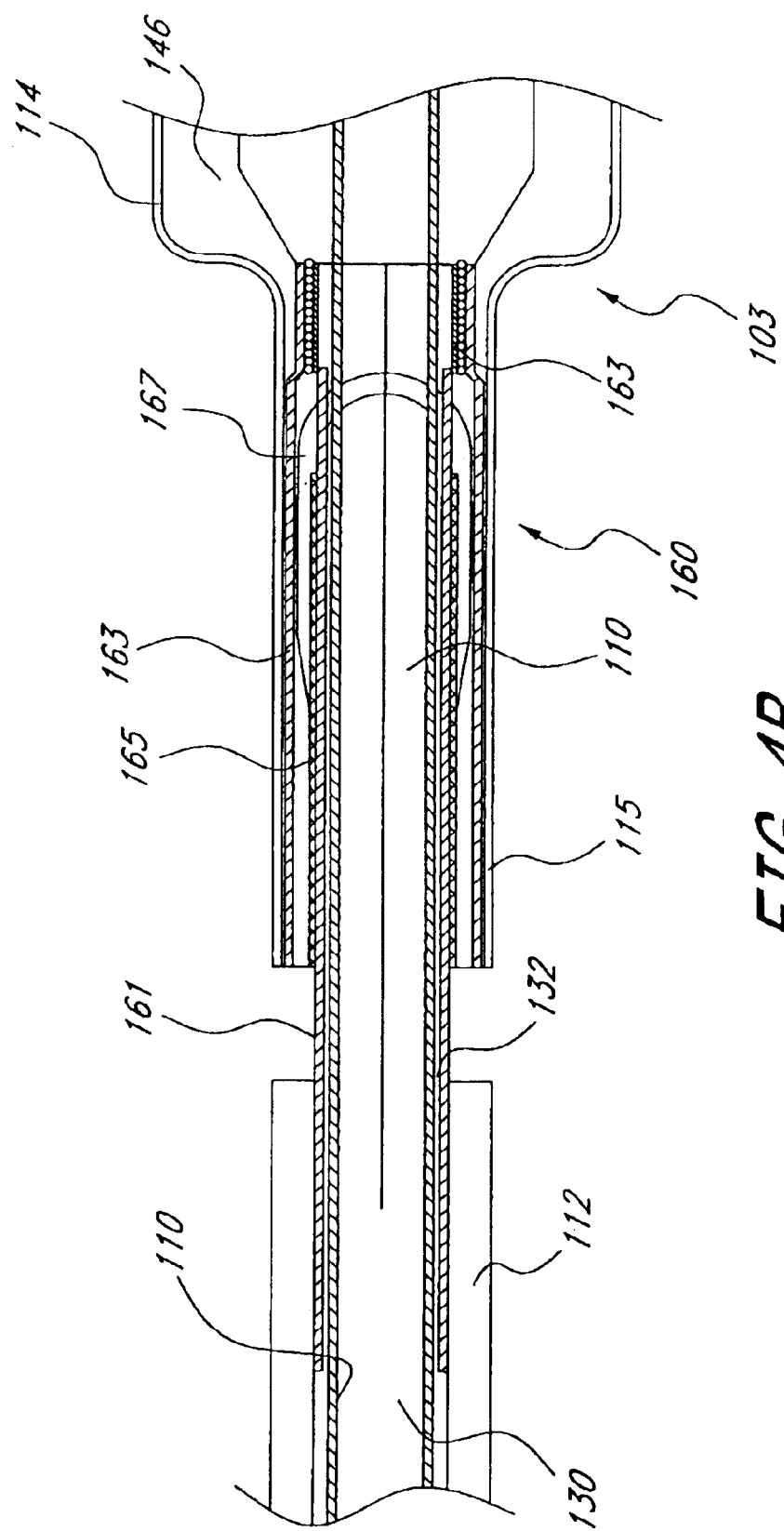
FIG. 4B is a detailed view of the inflatable fixation device of FIG. 4A.
Figure 4C:
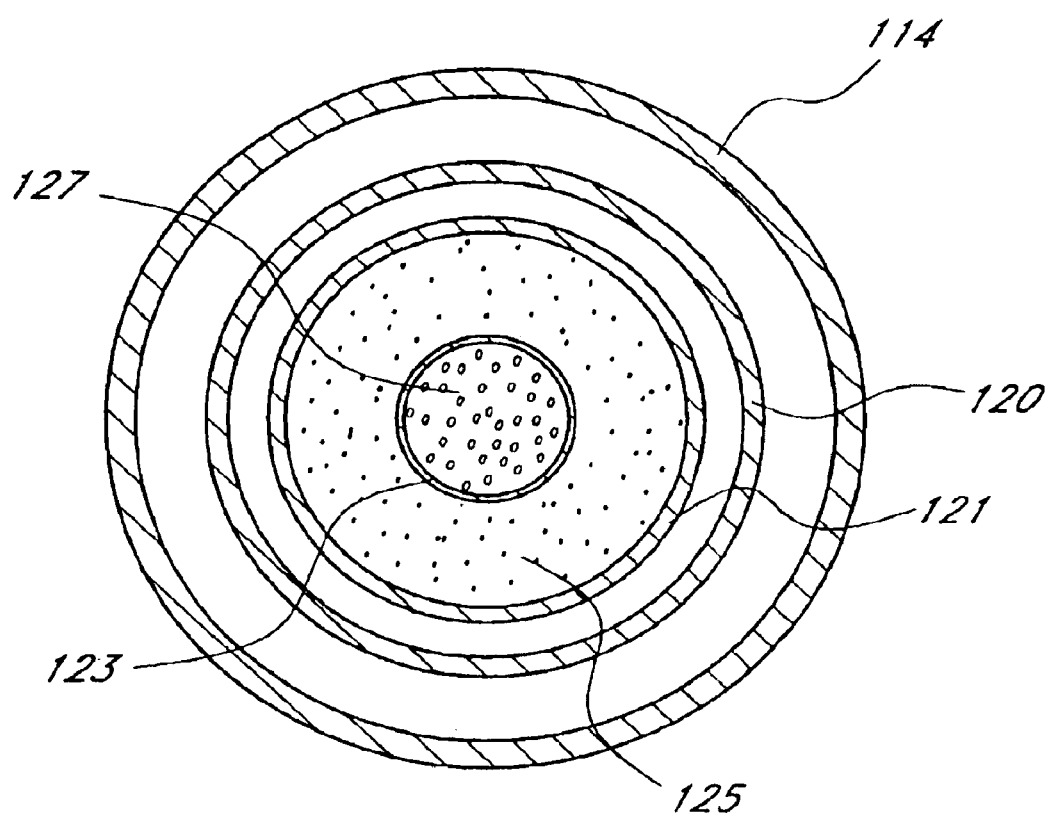
FIG. 4C schematically illustrates a cross-section through a composite formable rod in accordance with one aspect of the present invention.

One construction of a composite formable rod in accordance with the present invention is illustrated in FIG. 4C. An outer balloon or other containment structure 114 is provided, as has been discussed. A reinforcing element 120 such as a stent is concentrically positioned within the balloon. An outer support tube 121 is positioned within the stent in the illustrated embodiment, however, the outer support tube 121 can alternatively be positioned concentrically outside of the stent 120. The outer support tube 121, in one embodiment, is a 0.5 inch diameter braided carbon fiber tube, having cross strands oriented at 45° angles with respect to each other to improve torsion resistance as has been discussed.

An inner support tube 123 is spaced radially inwardly from the outer support tube 121. Inner support tube 123, in one embodiment, comprises a 0.3" diameter braided carbon fiber sleeve having characteristics described above. A first plurality of unidirectional fibers 125 is axially oriented within the annular space between the outer support tube 121 and inner support tube 123. A second plurality of unidirectional carbon fibers 127 is positioned within the inner support tube 123.

Any of a variety of alternate constructions can be readily utilized, in accordance with the teachings herein. For example, three or more tubular support tubes may be utilized. The layering sequence of the various components may be changed, and other features added or deleted depending upon the desired performance of the finished device. In addition, although the balloon 114 in one embodiment comprises a nylon single layer balloon, other materials may be utilized. In addition, multiple layer balloons may be utilized, with or without support structures such as stents, wires, or woven tubular support structures sandwiched therebetween.

Marker bands made of materials such as gold, platinum or tantalum may also be positioned on the balloon, to facilitate fluoroscopic visualization. Alternatively, a radio opaque material, such as tantalum powder, may be sprinkled among the carbon fibers prior to infusion of the epoxy or other hardenable media, to allow visualization during placement.

The epoxy or the polyurethane material preferably has a relatively fast cure rate at 37° C. A low viscosity (no greater than from about 100 to about 1000 CPS) facilitates rapid transluminal introduction through the delivery catheter and wetting of the relatively small intrastitial spaces between adjacent carbon fibers. In addition, the polymer is preferably radiopaque. The polymerization is preferably minimally exothermic, to minimize or prevent thermal damage to the surrounding tissue. One epoxy which may be useful in the present invention is Epotek 301. This epoxy reaches 50 to 60% of its strength within about three to four hours following deployment, at 37° C. Using a bonding agent having these approximate characteristics, the patient can be restrained from rolling for an initial cure period of approximately three or four hours to achieve a partial cure (e.g., at least about 50% and preferably 60% or more), and be maintained in bed for a secondary cure period such as approximately the next eight to twelve hours or more to accommodate a full cure. Other formulations of two part epoxies or polyurethanes with faster cure times (preferably no more than about one hour full cure) can be formulated by changing the ratios of components and formulations for the catalysts.

Terms such as "hardenable" or "curable" media are used interchangeably herein, and are intended to include any material which can be transluminally introduced through the catheter body into the cavity 146 while in a first, flowable form, and transitionable into a second, hardened form. These terms are intended to cover materials regardless of the mechanism of hardening. As will be understood by those of skill in the art, a variety of hardening mechanisms may exist, depending upon media selection, including UV, other wavelength of electromagnetic energy, or catalyst initiated polymerization, thermally initiated polymerization, solvent volatilization, and the like. While the media selection may affect catheter design in manners well understood by those of skill in the art, such as to accommodate outgasing of byproducts, application of heat, catalysts, or other initiating or accelerating influences, these variations do not depart from the concept of the invention of introducing a flowable media into a shape and subsequently curing the media to the shape. Two part medias, such as a two part epoxy or polyurethane, or a monomer and an initiator may be introduced into the cavity 146 through separate lumen extending throughout the tubular body. Expandable media may also be provided, such as a material which is implantable in a first, reduced volume, and which is subsequently enlargeable to a second, enlarged volume such as by the application of water or heat, or the removal of a restraint.

Various safety features to minimize the risk of rupture or leakage of the hardenable media may be utilized, depending upon design preferences. For example, a two-layer or three-layer or more balloon may be utilized to reduce the risk of rupture. In addition, the material of the single or multiple layers of the balloon may be selected to minimize escape of volatile components from the curable media. In one embodiment, a double balloon is provided having a nylon inside layer and a PET outside layer.

In addition, the inflation pressure of the curable media may be affected by the nature of the balloon. For example, a polyethylene balloon having a wall thickness of about 0.001" may have a burst pressure of about 7 to 8 atmospheres. In that embodiment, an inflation pressure of no more than about 4 to 5 atmospheres may be desired. A slightly higher inflation pressure, such as on the order of from about 5 to about 6 atmospheres, may be utilized with a nylon balloon. Relatively noncompliant materials such as PET have much higher burst pressures (range of 10–20 atmospheres), as is well understood in the balloon angioplasty arts.

In addition, the balloon contains a proximal valve as will be discussed in additional detail below. Multiple valves may be utilized, in series along the flow path, to reduce the risk of failure and escape of hardenable media. As a further safety feature, the deployment catheter may be provided with an outer spill sheath in the form of an elongate flexible tubular body which surrounds the deployment catheter and at least a proximal portion of the balloon. This spill sheath provides an additional removable barrier between the junction of the catheter and the balloon, and the patient. If a spill occurs during the filling process, the spill sheath will retain any escaped hardenable media, and the entire assembly can be proximally retracted from the patient. Following a successful filling of the balloon, the spill sheath and deployment catheter can be proximally retracted from the patient, leaving the inflated formable orthopedic fixation structure in place.

The reinforcing element 120 may be exposed to the interior cavity 146 formed by the flexible wall 148, providing additional structural integrity. See, e.g., FIGS. 1 and 4C. The reinforcing element 120 resists kinking of the balloon as the balloon is advanced around corners such as during advancement through an aperture (e.g., portal or eyelet) on a bone anchor. The reinforcing element 120 may be positioned within the balloon 114. The reinforcing element may alternatively be embedded within the wall of the balloon 114, or carried on the outside of the balloon much like a conventional stent. The reinforcing element 120 may be an expandable tube, a slotted metal tube, reinforcing wires, straight, woven or braided fibers such as carbon fibers, or a stent. Certain preferred embodiments may include a tube and wire. Reinforcement element 120 may comprise thin, reinforcing metallic wires, separate from the balloon wall. The wires increase the tensile strength of balloon 114 when inflated. Wires may be titanium, nitinol, elgiloy, or any other suitable material as known to those of skill in the art.

The reinforcement element 120 may include an expandable tubular stent. A stent of any suitable type or configuration may be provided with the delivery device, such as the Cordis artery stent ("smart stent"). Various kinds and types of stents are available in the market (Sulzer/Medica "Protege" stent and Bard "Memotherm" stent), and many different currently available stents are acceptable for use in the present invention, as well as new stents which may be developed in the future.

Referring to FIGS. 4A and 4B, the illustrated elongate tubular body 104 comprises an outer sleeve 112 and an inner sleeve 110 movably positioned within the outer sleeve 112. The inflatable device 102 is removably carried by or near the distal end 108 of the outer sleeve 112. Alternatively, the inflatable device 102 may be removably carried by the inner sleeve 110. The inner sleeve 110 may extend into the inflatable device 102, as illustrated.

The balloon 114 may be removably attached to the tubular body 104 by a slip or friction fit on the distal end 108 of the outer sleeve 112 or on the inner sleeve 110. A variety of alternative releasable attachments may be used between the outer sleeve 112 and/or inner sleeve 110 and the proximal end 103 of the balloon 114, such as threaded engagement, bayonet mounts, quick twist engagements like a luer lock connector, and others known in the art. In each of these embodiments, a first retention surface or structure on the outer sleeve 112 and/or inner sleeve 110 releasably engages a complimentary surface or retention structure on the proximal end 103 of the balloon 114 as will be apparent to those of skill in the art.

The balloon 114 comprises a self-sealing valve 160 which prevents the hardenable media from leaking once the delivery catheter 100 is detached from the balloon 114. Valve 160 is provided for closing the pathway between inflation lumen 130 and inner cavity 146. Valve 160 may be located at the proximal end 116 of inflatable device 102. A variety of different valves may be used as will be recognized by those of skill in the art, such as a slit valve, check valve, duckbilled or flap valve. Alternatively, a stopper may be provided which can be placed within the pathway to prevent leakage.

Referring to FIG. 7A, a duck bill valve is schematically illustrated. This valve includes at least a first, and preferably two or more coaptive leaflets 161 and 163, which incline towards each other in the distal direction as will be understood by those of skill in the art. Distal advancement of the inner sleeve 110 and/or pressurized media through the valve 160 forces the coaptive leaflets 161 and 163 apart, to facilitate introduction of the hardenable media. Upon removal of the inner sleeve 110, the coaptive leaflets 161 and 163 return to a closed configuration to inhibit or prevent the escape of hardenable media. A single leaflet 161 may be utilized, in the form of a flapper valve.

An alternate valve is illustrated in FIGS. 7B and 7C, and in an assembled device in FIG. 4B. In this valve, a tubular support structure 165 is provided with a closeable cap 167. The closeable cap 167 may be formed from any of a variety of highly flexible polymeric materials, such as silicone, neoprene, latex, or others known in the art. Cap 167 may be formed such as by dip molding or liquid injection molding, followed by the provision of a slit or potential opening 169.

The valve 160 may be connected to or formed with the inflatable device in any of a variety of manners, as will be appreciated in view of the disclosure herein. In the illustrated embodiment, the balloon 114 is provided with a proximally extending neck 115 which carries the valve 160 therein. The tubular body 165 having the cap 167 thereon is positioned concentrically within the proximal neck 115, as illustrated in FIG. 4B. Alternatively, the valve 160 may be positioned within the balloon 114, i.e., distally of the proximal shoulder of the balloon 114.

Additional details of one detachable connection between the delivery system and the implantable device is illustrated in FIG. 4B. As illustrated therein, a tube 161 extends distally from the outer sleeve 112. Tube 161 may comprise any of a variety of materials, which exhibit sufficient structural integrity for the intended use. In one embodiment, tube 161 is a metal hypotube having an inside diameter of about 0.085" to about 0.086 and a wall thickness of about 0.001" to about 0.002". The tube 161 in the illustrative embodiment extends for a distance of about 0.50 mm to about 0.75 mm beyond the distal end of the outer sleeve 112.

The tube 161 extends into a sliding fit with a tubular support structure 163 which may be positioned in a proximal neck portion of the balloon. When positioned as illustrated, the tube 161 ensures that the valve 160 is open, so that the inner sleeve 110 may extend axially therethrough into the balloon.

In addition, the inside diameter of the tube 161 is preferably sufficiently larger than the outside diameter of the inner sleeve 110 to provide an annular passageway in communication with the vent lumen 132. This structure ensures that the interior of the balloon remains in communication with the proximal vent port by way of a vent lumen 132 extending throughout the length of the assembly. In the illustrated embodiment, the outside diameter of the inner sleeve 110 is about 0.082" to about 0.084", and the inside diameter of the tube 161 is about 0.085" to about 0.086". Following infusion of the curable media into the balloon, the inner tube 110 and tubular body 161 are both proximally retracted from the balloon, thereby enabling the valve 160 to close as is described elsewhere herein.

When fully inflated, as shown in FIG. 6, the balloon 114 has an inflated profile with a cylindrical working portion 140 having an inflated diameter located between a pair of conical end portions 142, 144.

Figure 9:
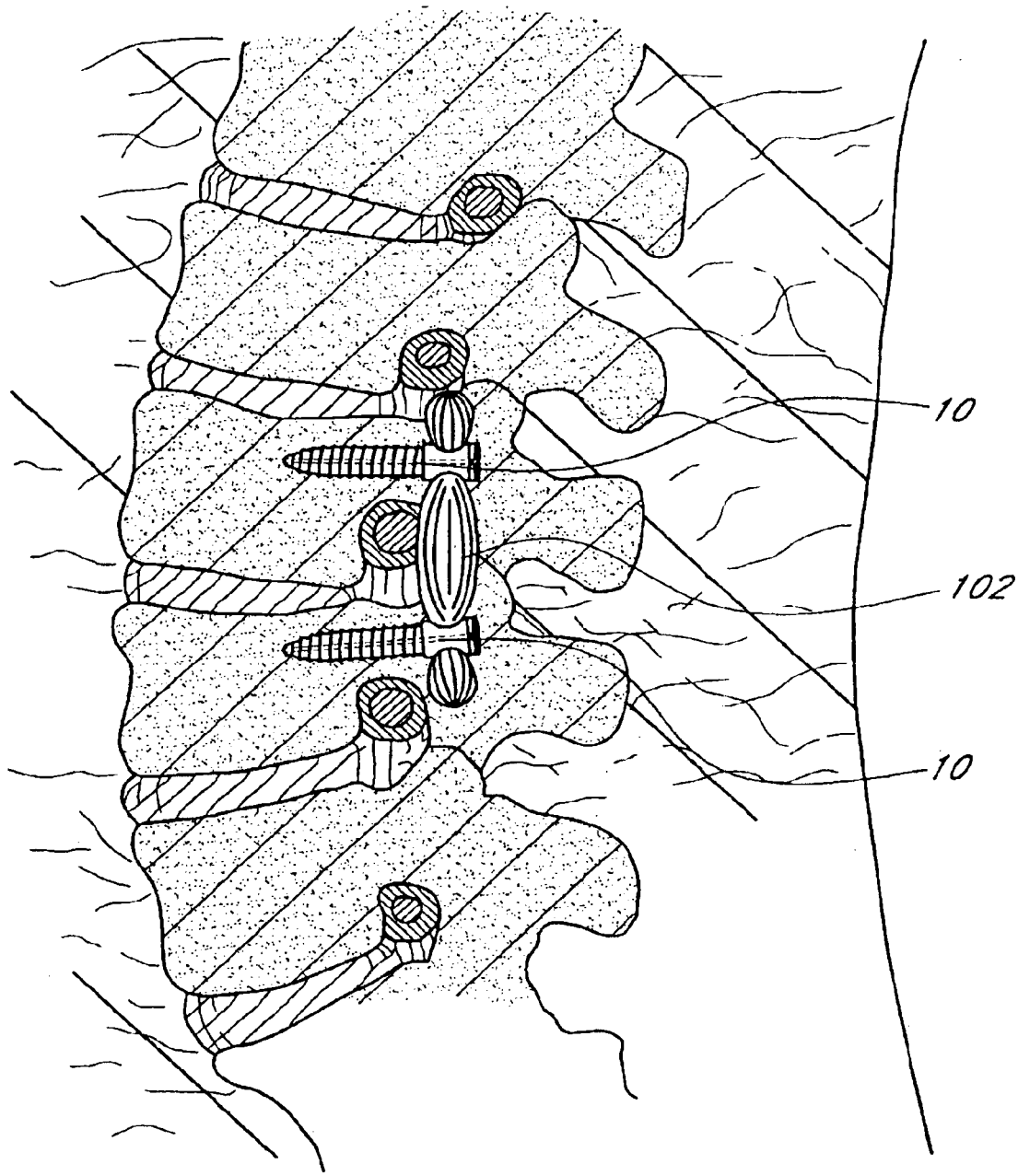
FIG. 9 is a side elevational view of a portion of the spine, having a formable orthopedic fixation system implanted therein.
Figure 10:
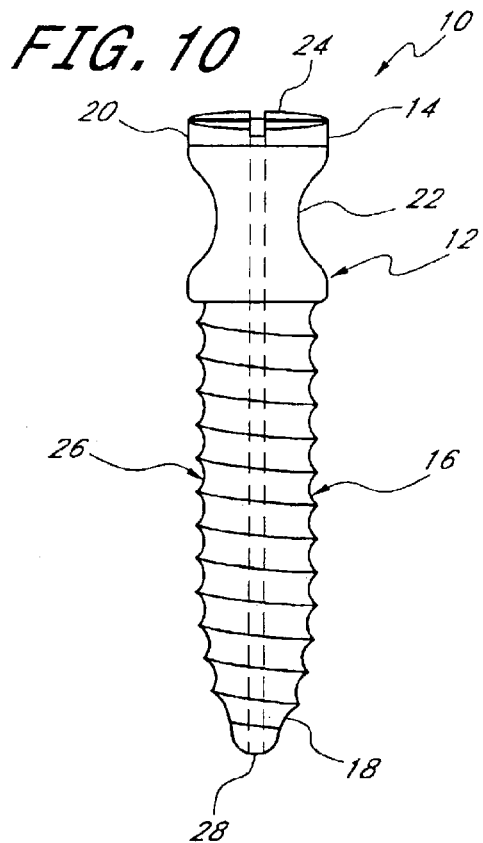
FIG. 10 is a side elevational view of a bone anchor.
Figure 11:
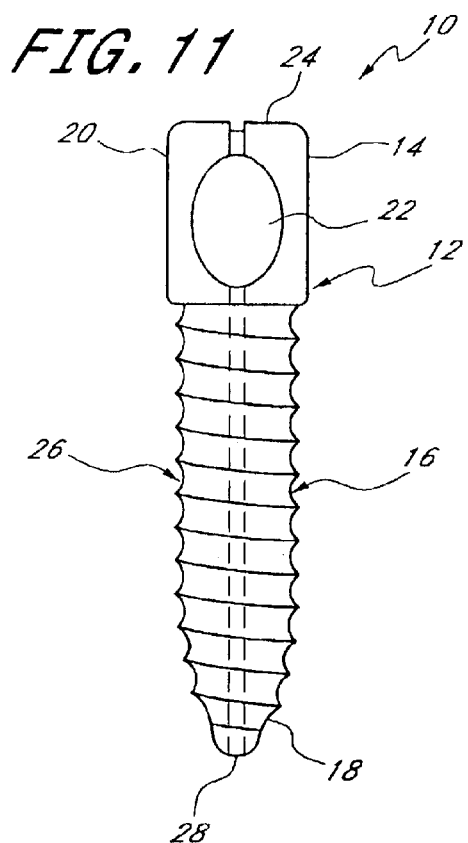
FIG. 11 is a side elevational view of the bone anchor of FIG. 10, rotated 90° about its longitudinal axis.
Figure 12:
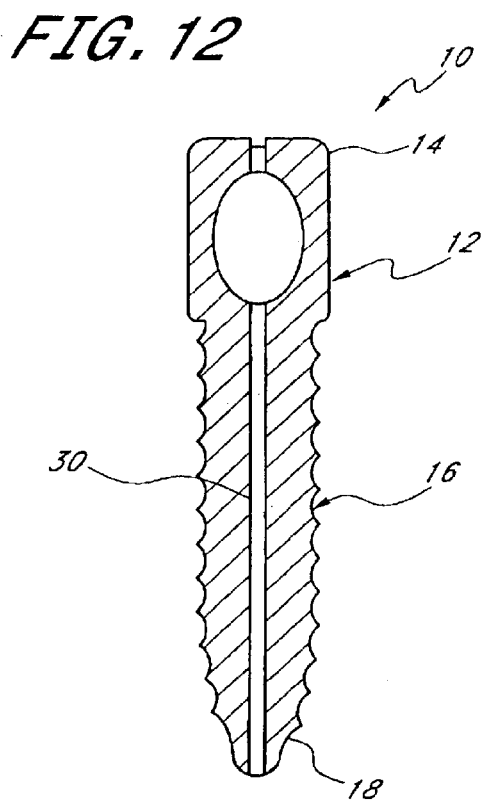
FIG. 12 is a longitudinal cross-sectional view of the bone anchor of FIG. 11.
Figure 13:
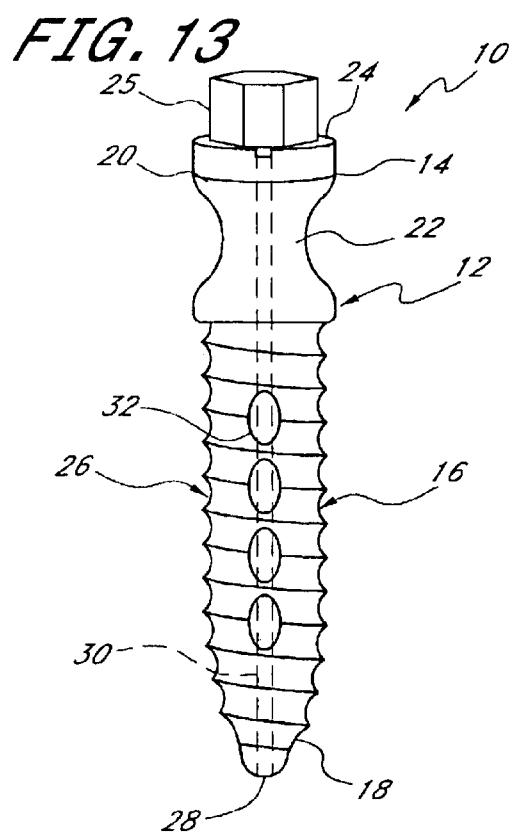
FIG. 13 is a side elevational view of an alternative embodiment of a bone anchor, with bone ingrowth apertures.

Referring to FIG. 9, at least one bone anchor 10 may be provided, such as that shown in FIG. 10. The bone anchor 10 includes a first aperture 22, through which the orthopedic device 102 extends. A second bone anchor 10 may also be provided including a second aperture 22, through which the orthopedic device 102 also extends. The first bone anchor 10 is preferably implanted within a first bone. The second bone anchor 10 may be implanted within the second bone. The bones may be adjacent vertebrae or first and second vertebrae spaced apart by one or two or more intermediate vertebrae.

The bone anchors of FIGS. 10–13 are made of a biocompatible material such as titanium or stainless steel. Alternatively, bone anchors 10 may be made of a composite material. Bone anchors 10 may also be made of a suitable medical grade polymer. In one embodiment, bone anchors 10 have a length between about 40 mm and 60 mm, preferably about 50 mm. However, the actual length is dependent on location of the fracture, size of patient, etc.

Bone anchor 10 comprises a proximal portion 12 having a proximal end 14 and a distal portion 16 having a distal end 18. Proximal portion 12 typically comprises a head 20 and a portal 22. In a preferred embodiment, head 20 comprises a proximal portion 24 configured to mate with the tip of a screwdriver. Head 20 may comprise a standard or Phillips slot for mating with the screwdriver. A variety of slot configurations are also suitable, such as hexagonal, Torx, rectangular, triangular, curved, or any other suitable shape. The bone anchor of FIG. 13 has a raised platform 25 having a plurality of substantially straight sides, such as a hexagonal platform, configured to mate with a corresponding depression in the distal end of a screwdriver. Platform 25 may come in a variety of shapes suitable mating with a screwdriver.

Portal 22 of bone anchor 10 may extend through head 20 and is generally between about 4 mm and 8 mm in diameter, preferably about 6 mm to about 8 mm in diameter. Portal 22 may be of any shape suitable for receiving inflatable, implantable orthopedic device 102; however, portal 22 is preferably round.

Figure 14:
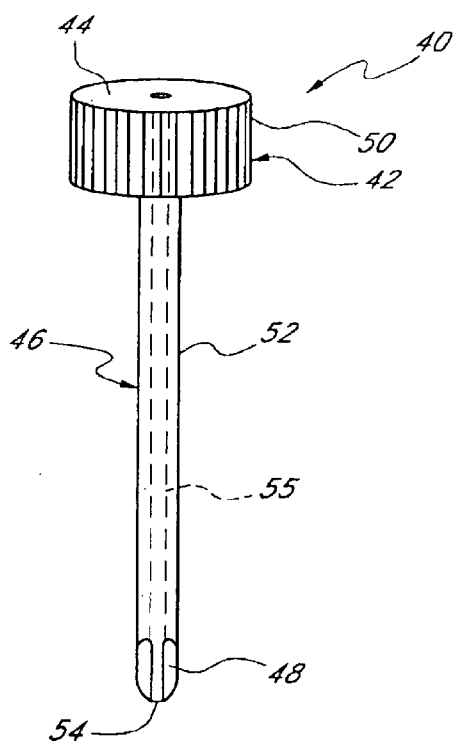
FIG. 14 is a side elevational view of a screwdriver.

Distal portion 16 of bone anchor 10 typically comprises threads 26 and a sharp tip 28. Bone anchor 10 also preferably comprises a central lumen 30 extending coaxially completely through bone anchor 10 from proximal end 14 to distal end 18 and configured to receive a guidewire. Bone anchor 10 may also include at least one perforation 32, as shown in FIG. 14. Perforation 32 may be aligned axially, as shown, or may be staggered axially. Perforation 32 permits bone to grow into bone anchor 10, stabilizing bone anchor 10 within the bone. Additionally, bone matrix material such as a hydroxyapatite preparation can be injected into central lumen 30 and through perforation 32 to promote bone in-growth.

Figure 15:
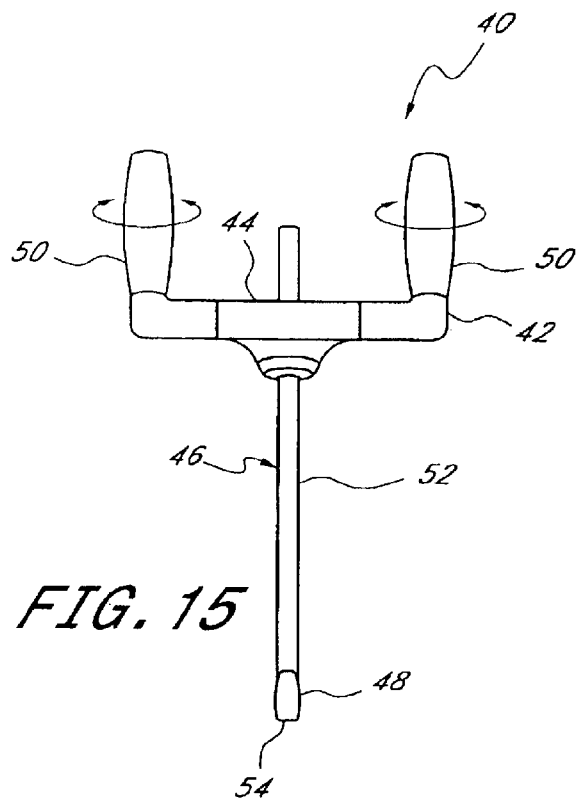
FIG. 15 is a side elevational view of an alternative embodiment of a screwdriver.

FIGS. 14 and 15 show screwdrivers 40 configured to apply torque to bone anchor 10. Screwdriver 40 comprises a proximal portion 42 having a proximal end 44 and a distal portion 46 having a distal end 48. Proximal portion 42 includes a handle 50 configured to permit grasping to apply torque to anchor 10. Various configurations of proximal end 44 are possible. In the embodiment of FIG. 15, the proximal handles 50 may be independently rotatable about their longitudinal axes.

Distal portion 46 comprises a shaft 52 having a tip 54 configured to interface with proximal portion of bone anchor 10. Screwdriver 40 may also comprise a central lumen 55 extending coaxially from proximal end 44 to distal end 48 configured to receive a guidewire.

Figure 16:
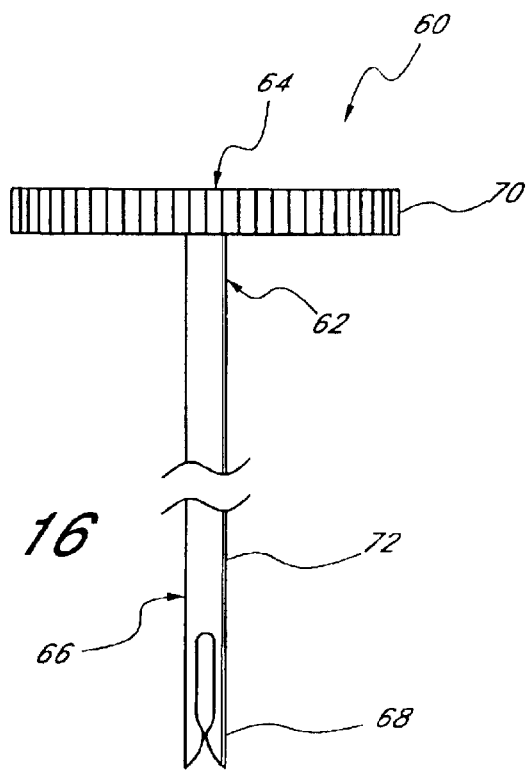
FIG. 16 is a side elevational view of a guidewire directing device.

FIG. 16 shows a guidewire directing device 60, which may be used percutaneously to alter the direction of an advancing guidewire. Guidewire directing device 60 comprises a proximal portion 62 having a proximal end 64 and a distal portion 66 having a distal end 68. Proximal portion 62 comprises a handle 70. Handle 70 is configured to assist in grasping and manipulating guidewire directing device 60. The distal portion 66 comprises a shaft 72 having a fork-tipped end 68. Guidewire directing device 60 engages a guidewire at the fork-tipped end 68. Handle 70 is rotated, advanced, and withdrawn, thereby altering the direction of the advancing guidewire.

Figure 17:
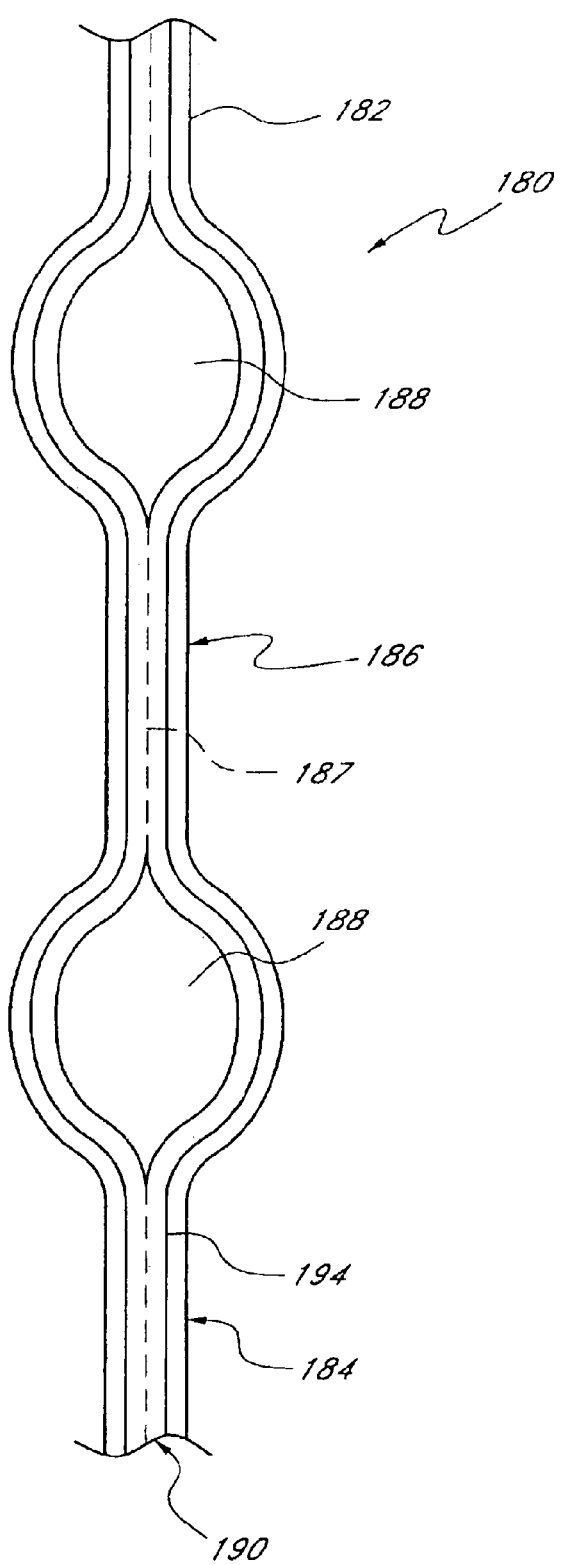
FIG. 17 is a top plan view of a directing sheath.

A directing sheath 100, as shown in FIG. 17, may also be provided for assisting in aligning the guidewire or delivery catheter to pass through bone anchors 10. Directing sheath 100 comprises a proximal portion 102, a distal portion 104, and a central portion 106. Central portion 106 includes at least two openings 108 sized substantially the same as portal 22 of bone anchor 10. Directing sheath 100 preferably includes a lumen 110 extending through its entire length. Lumen 110 is of sufficient diameter to allow a structure such as a guidewire or delivery catheter to pass through. Directing sheath 100 may be scored along its longitudinal axis, on either one line or two opposing lines 112. Scoring 112 allows directing sheath 100 to be split into two separate halves by pulling the sheath apart at its proximal or distal end. Scoring 112 can be partially or completely through the sheath wall.

Directing sheath 100 is preferably formed from a biocompatible polymer. Directing sheath 100 may also include a radiopaque filament 114 passing around each opening in central portion 106 or the entire length of sheath 100. Filament 114 aids in localizing directing sheath 100 after percutaneous placement.

Although the application of the present invention will be disclosed in connection with connecting two unstable vertebrae, the methods and structures disclosed herein are intended for various other applications such as to connect three or more vertebrae, as will be apparent to those of skill in the art in view of the disclosure herein. In addition, the method may be used to stabilize the L5 vertebrae, using the cranial-ward portion of the sacrum as the vertebrae with which L5 is anchored. Furthermore, although the method is disclosed and depicted as applied on the left side of the vertebral column, the method can also be applied on the right side of the vertebral column, or both sides of the vertebral column simultaneously.

The method of the present invention involves percutaneously inserting one or more fusion devices into two or more than two adjacent vertebrae, either unilaterally or, preferably bilaterally, where a portion or all of at least one of the vertebrae is unstable, separated or displaced. The fusion devices reposition or fix the displaced vertebra or portion of the displaced vertebra to a position within the vertebral column which is more stable or which causes less morbidity.

Referring now to FIG. 18 through FIG. 28, there are shown a series of drawings depicting various stages of the method of repositioning and fixing a displaced vertebra or portion of a displaced vertebra, unilaterally, according to the present invention. FIGS. 18–28 show partial cutaway, perspective, midline sagittal views of a portion of a vertebral column undergoing the method of the present invention.

The method will now be disclosed and depicted with reference to only two vertebrae, one which is either unstable, separated or displaced and one of which is neither unstable, separated nor displaced. However, the method can also be applied to three or more vertebrae simultaneously, as will be understood by those with skill in the art with reference to this disclosure. Additionally, the method can be used to stabilize the L5 vertebrae, using the cranial-ward portion of the sacrum as the "vertebrae" with which L5 is anchored. Further, though the method is disclosed and depicted as applied on the left side of the vertebral column, the method can also be applied on the right side of the vertebral column or, preferably, can be applied on both sides of the vertebral column, as will be understood by those with skill in the art with reference to this disclosure.

First, the present method comprises identifying a patient who is a suitable candidate for undergoing the method. A suitable candidate has one or more unstable vertebrae, one or more portions of one or more vertebrae at least partly separated from the remainder of the vertebrae, one or more portions of one or more vertebrae at least partly separated from the remainder of the vertebrae with potential or complete separation, or has one or more vertebrae or a portion of one or more vertebrae displaced from its normal position relative to the vertebral column, or has one or more portions of one or more vertebrae at least partly separated from the remainder of the vertebrae and displaced from its normal position relative to the vertebral column. Further, the suitable candidate will preferably have either pain, loss of function or real or potential instability which is likely due to the separation or displacement, or separation and displacement. If only a portion of the vertebra is unstable, separated or displaced, the portion of the vertebra that is unstable, separated or displaced will generally include at least part of the vertebral body and adjoining pedicle. However, other unstable, separated or displaced portions of a vertebra can be repositioned or fixed using the present method, as will be understood by those with skill in the art with reference to this disclosure. For example, a suitable patient can have a disease or condition such as spondylosis, spondylolisthesis, vertebral instability, spinal stenosis and degenerated, herniated, or degenerated and herniated intervertebral discs, though actual indications require the expertise of one of skill in the art as will be understood by those with skill in the art with reference to this disclosure.

Next, the present method comprises making a stab incision in the patient's skin overlying the patient's vertebral column at or near the level of the vertebrae or portion of vertebrae to be repositioned or fixed. In one embodiment, the incision is made at or near the level of the pedicle of the vertebra or portion of vertebra to be repositioned or fixed. The pedicle level is located preferably by identifying the pedicle shadow using fluoroscopy. In a preferred embodiment, the stab incision is made using a #11 scalpel blade.

Figure 18:
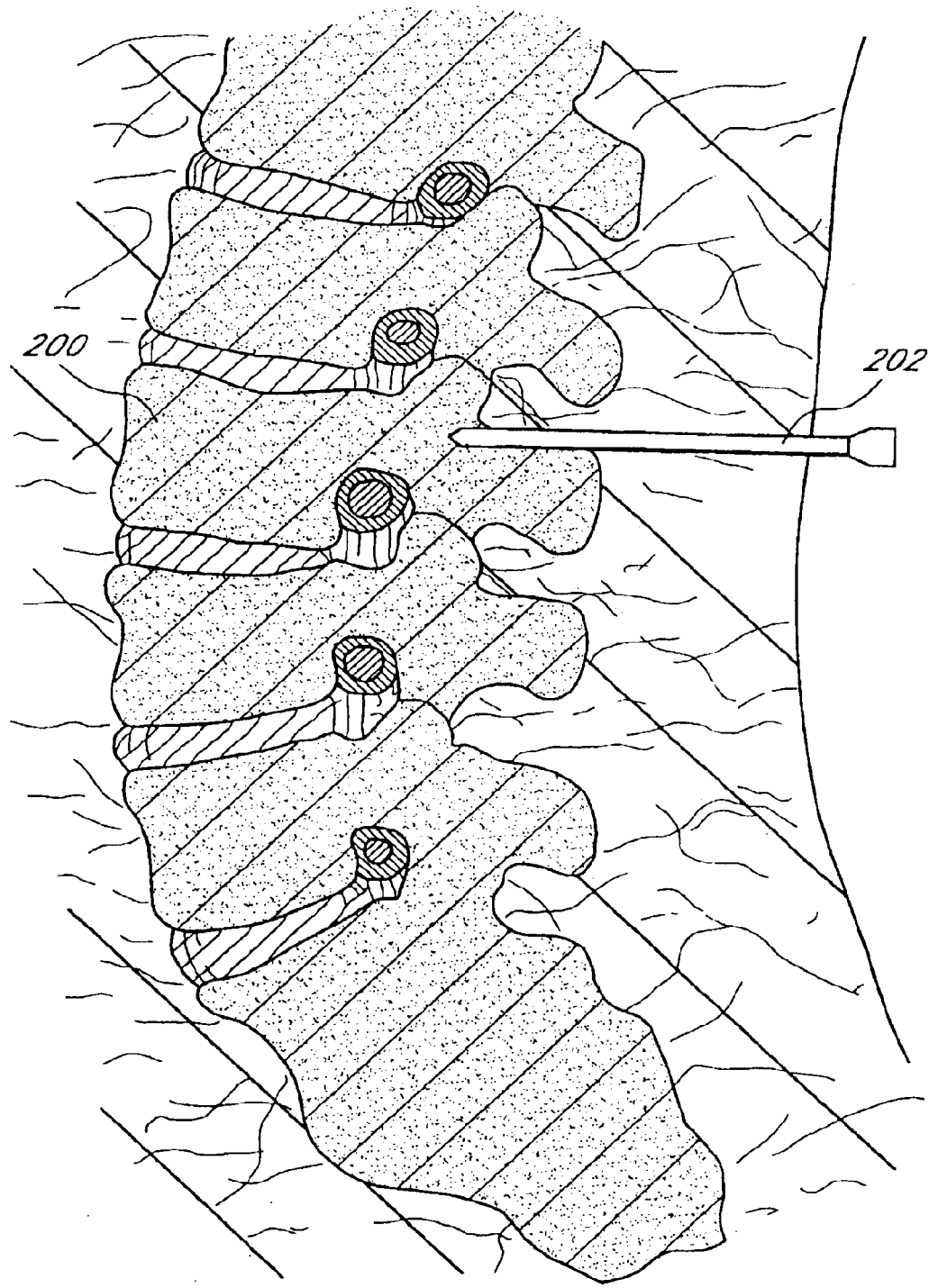
FIGS. 18–28 are partial cross-sectional midline sagittal views of a portion of a vertebral column showing an implantation method of the present invention.

Then, as shown in FIG. 18, an 11-gauge bone biopsy needle 202 or its equivalent is placed through the stab incision to create a tract to the posterior periosteal surface of the vertebrae 200 which is to be stabilized, repositioned or fixed. Next, the biopsy needle 202 is used to make a small incision in the periosteum and into the cortex of the vertebrae.

Figure 19:
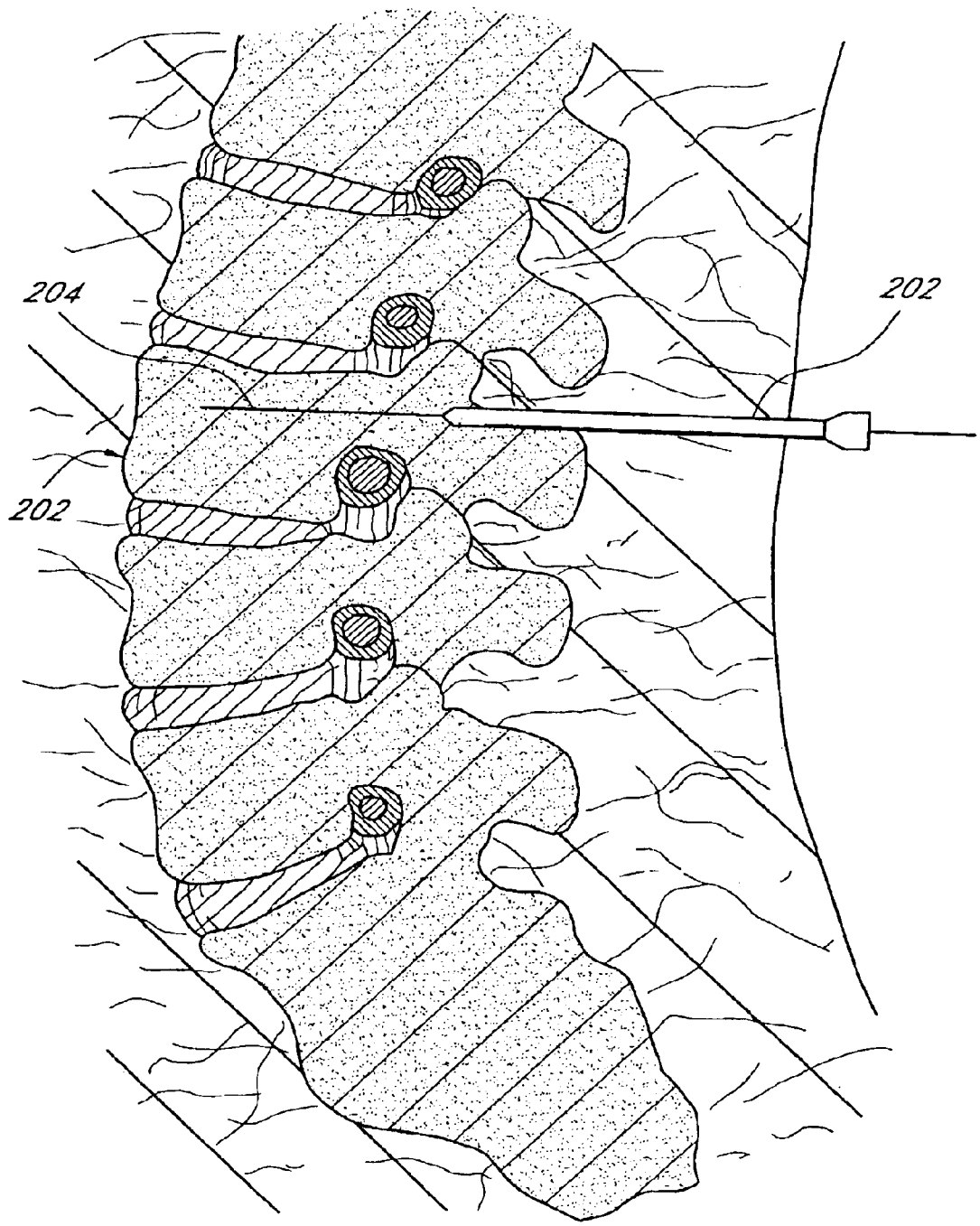

Then, as shown in FIG. 19, a rigid, needle-tipped guidewire 204 having a diameter in the range of 0.035" to about 0.060" is inserted though the biopsy needle 202 into the tract, through the periosteal incision and into the cortex of the bone, and the guidewire 204 is advanced into the anterior aspect of the vertebral body 200 or into another suitable portion of the vertebrae 200, as will be understood by those with skill in the art with reference to this disclosure. Insertion of the guidewire 204 is preferably accomplished using fluoroscopy. This process creates a continuous tract from the skin surface into the anterior vertebral body or suitable portion of the vertebrae 200.

The biopsy needle 202 is then removed and the tract from the skin surface to the nicked periosteal surface is enlarged by using a high-pressure fascial dilator balloon (not shown) over the needle-tipped guidewire. Then, the balloon is removed and a working sheath 206 is introduced into the dilated tract. Alternately, a hard plastic or metallic sheath with a central dilator is advanced over the guidewire from the skin surface to the periosteal surface. Next, a pilot hole may be drilled using an over-the-wire drill bit driven by a hand held drill.

Figure 20:
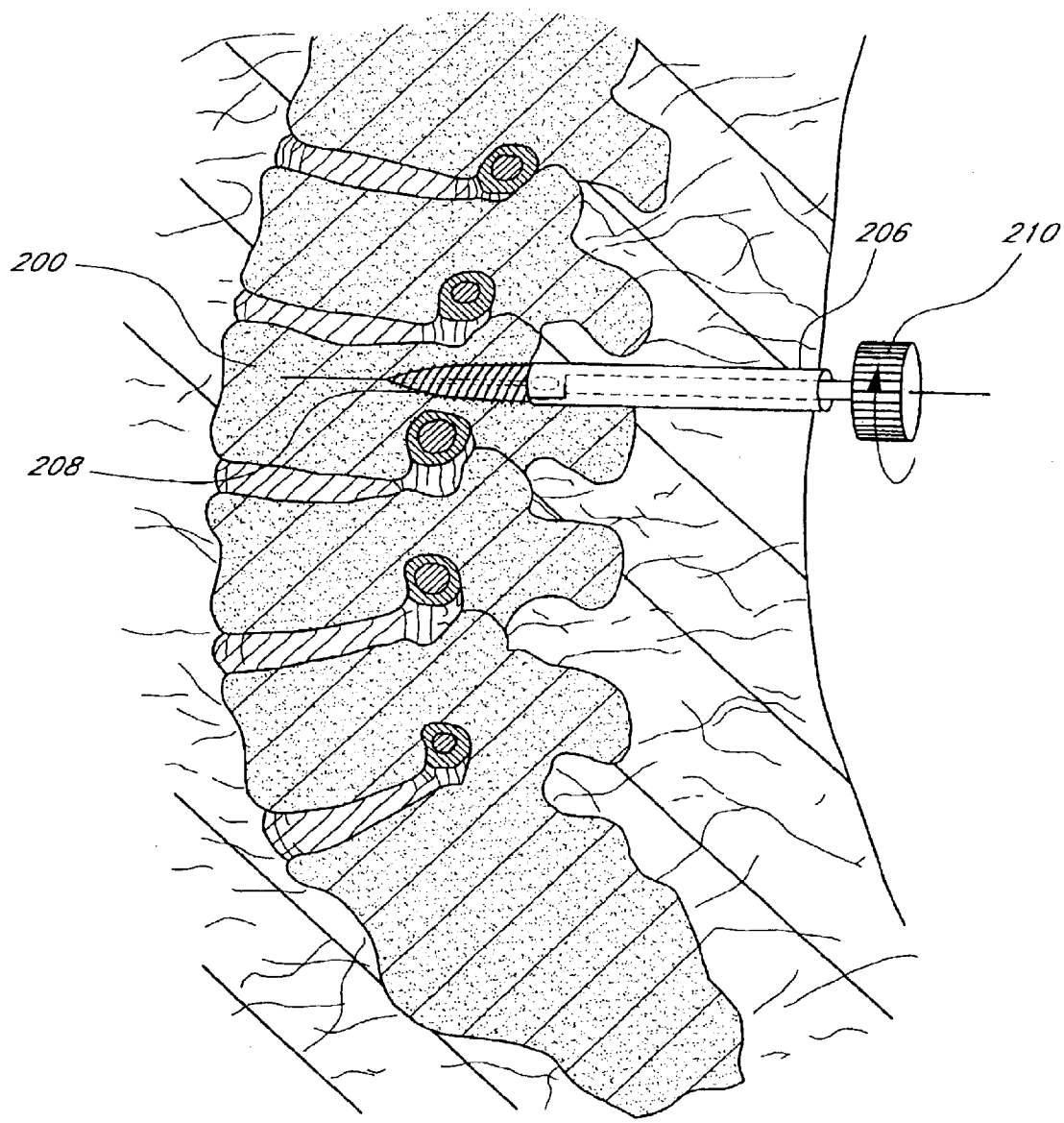
Figure 21:
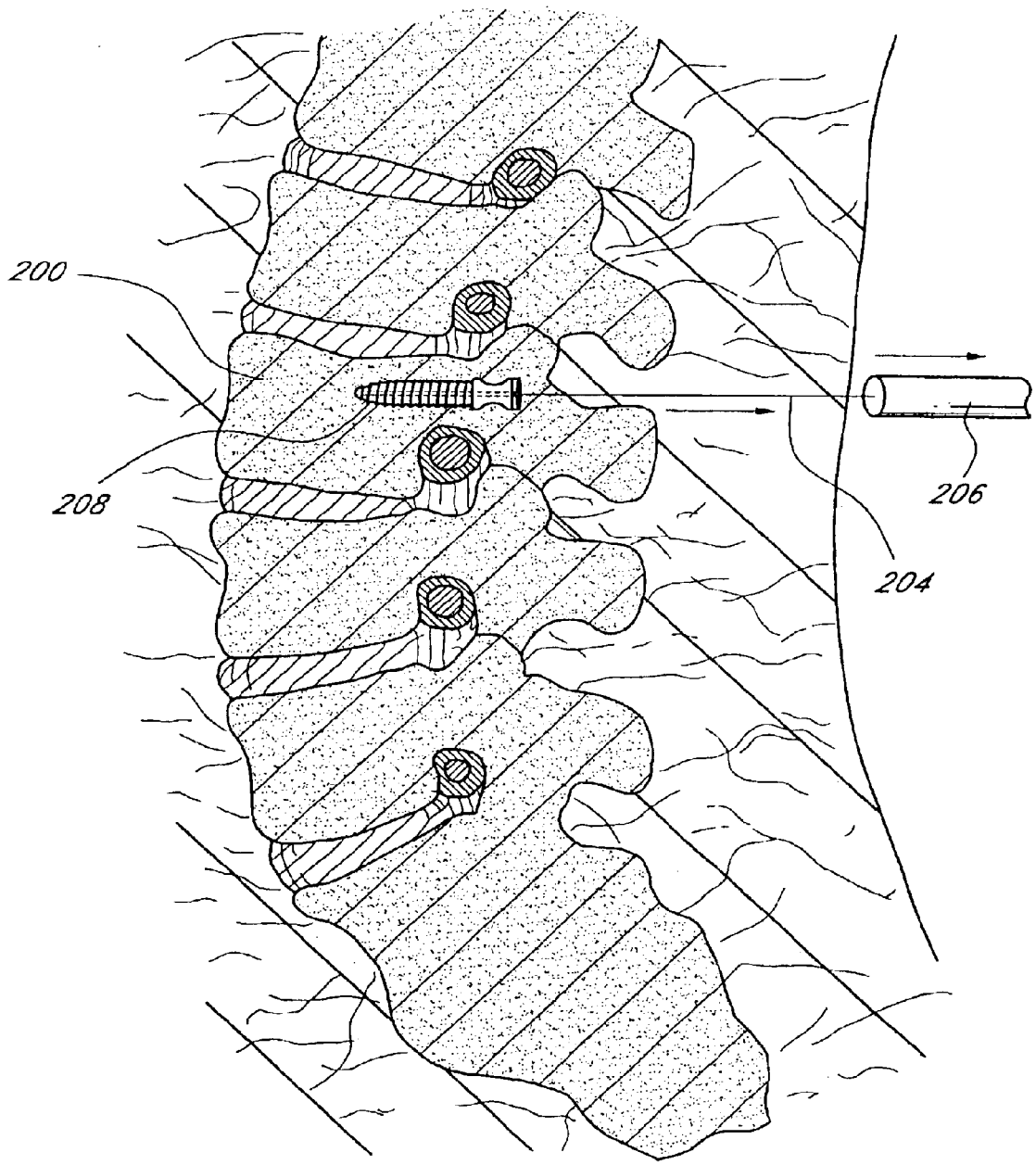

Next, as shown in FIG. 20, a bone screw 208 according to the present invention is introduced into the working sheath 206 over the guidewire 204 by introducing the central lumen of the bone screw 208 over the proximal end of the guidewire 204. A screwdriver 210 according to the present invention is similarly introduced over the guidewire 204. The bone screw 208 and distal portion of the screwdriver 210 are then advanced distally through the sheath 206 and the tract to the periosteal surface of the vertebral 200 until the proximal portion of the bone screw 208 using is engaged by the tip of the screwdriver 210. Torque is applied to the bone screw 208 using the screwdriver 210 and the bone screw 208 is advanced until the distal portion of the bone screw 208 enters the anterior vertebral body or other suitable portion of the vertebra 200, while the portal of the bone screw 208 is exterior and dorsal to the vertebra 200 and the portal is open parallel to the long axis of the vertebral column. Then, as shown in FIG. 21, the guidewire 204, sheath 206 and screwdriver 210 are removed after satisfactory placement of the bone screw 208 has been obtained and confirmed by fluoroscopy. Additionally, bone matrix material such as a hydroxyapatite preparation can be injected into the central lumen of the bone screw and through the one or more than one perforation, if present, to promote bone ingrowth.

The stages discussed above are repeated for at least one additional vertebra 212 until each vertebra that is to be repositioned or fixed has a bone screw 208 applied, and additionally for at least one vertebra which is neither unstable, separated nor displaced and which lies adjacent the cranial-most or caudal-most vertebra that is being repositioned or fixed. The bone screw 208 placed into the vertebra 212 which is neither unstable, separated nor displaced is used as the anchor to reposition or fix each vertebra 200 which is unstable, separated or displaced as follows. As will be understood by those with skill in the art with reference to this disclosure, the bone screws can be placed into the vertebrae in a different order to that described above.

After a bone screw is positioned in each vertebra, the portals are connected using an inflatable connection rod according to the present invention where the rod is inserted between the portals of the bone screws and inflated to create a rigid structure with the bone screws, thereby repositioning and fixing the one or more than one previously unstable, separated or displaced vertebra, or one or more previously unstable, separated or displaced portions of one or more vertebrae with the vertebra that is neither unstable, separated nor displaced. Connection of the bone screws with the inflatable rod is accomplished as follows.

Figure 22:
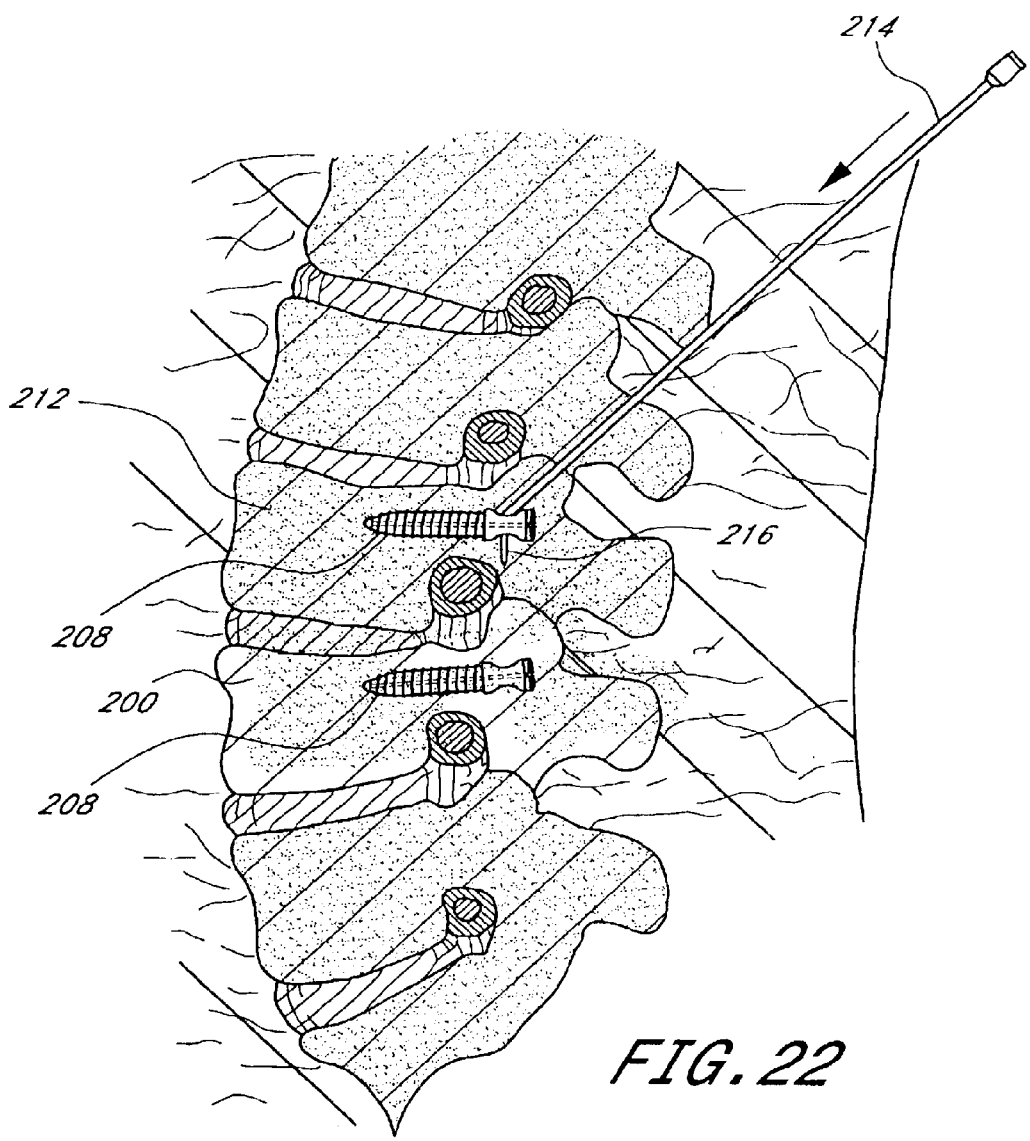
Figure 23:
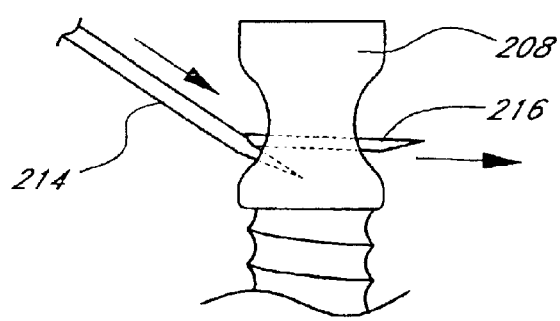

Referring now to FIG. 22 and FIG. 23, a hollow needle 214, such as a 16 gauge or 18 gauge needle, is inserted percutaneously and fluoroscopically advanced to the portal of one of the bone screws 208. While the hollow needle is shown engaging the bone screw 208 in the cranial-ward vertebrae 212, the hollow needle can engage the bone screw 208 in the caudal-ward vertebra 200 first, as will be understood by those with skill in the art with reference to this disclosure. FIG. 23 is a detailed view of FIG. 22.

Figure 24:
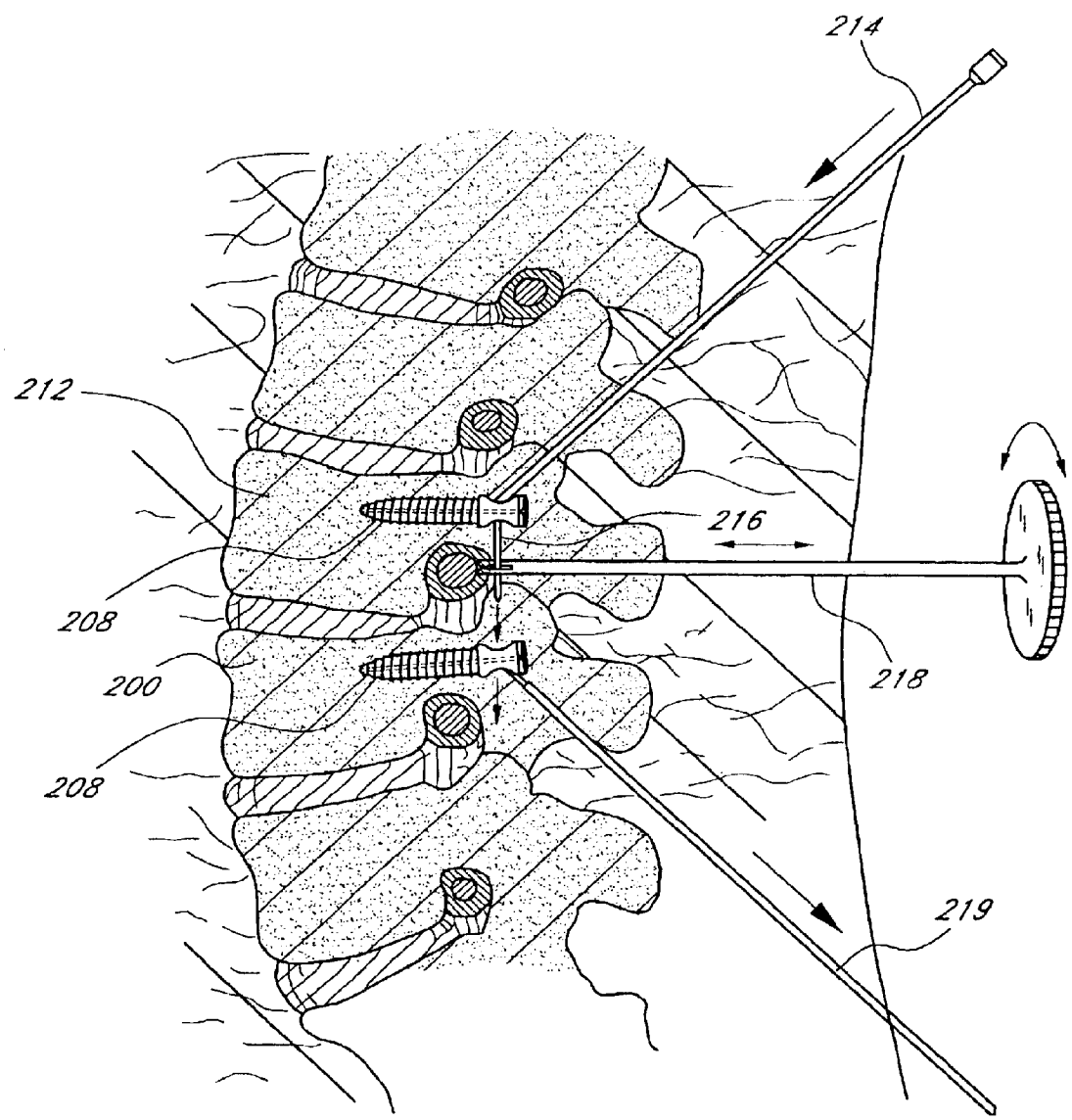

Then, as shown in FIG. 24, a needle-tipped, semi-rigid guidewire 216 is introduced through the lumen of the hollow needle 214 and into the portal of the bone screw 208 in the cranial-ward vertebrae 212. The hollow needle 214 preferably has a Tuohy needle tip which causes the guidewire 216 to exit the hollow needle 214 perpendicular to the distal-proximal axis of the bone screw 208 and parallel to the long axis of the vertebral column. Alternately, the hollow needle 214 can have an angled-tip modified Ross needle or other suitable structure as will be understood by those with skill in the art with reference to this disclosure.

In one embodiment, as further shown in FIG. 24, a guidewire directing device 218 according to the present invention is inserted percutaneously between the portals of each bone screw 208 and the fork-tipped end is used to direct the advancing guidewire 216 through the second bone screw portal, and to reorient the guidewire 216 after the guidewire 216 has passed through the portal on the bone screw 208 of the caudal-ward vertebrae 212.

In another embodiment, as further shown in FIG. 24, a guidewire capture device 219, such as a snare or grasping forceps, is inserted percutaneously, caudal to the portal of the bone screw in the caudal-ward vertebrae. The capture device 219 engages the guidewire after it passes through the portal of the bone screw in the caudal-ward vertebra and allows the distal end of the guidewire to be pulled through the skin posteriorly to obtain control of both the proximal and distal ends of the guidewire.

In another embodiment, the needle-tipped, semi-rigid guidewire 216 comprises an outer helical, flat wire sheath and an inner retractable sharp tip stylet. Once the needle-tipped, semi-rigid guidewire is placed, the stylet can be removed to allow for easier capture by the capture device with less trauma to the surrounding tissue.

Figure 25:
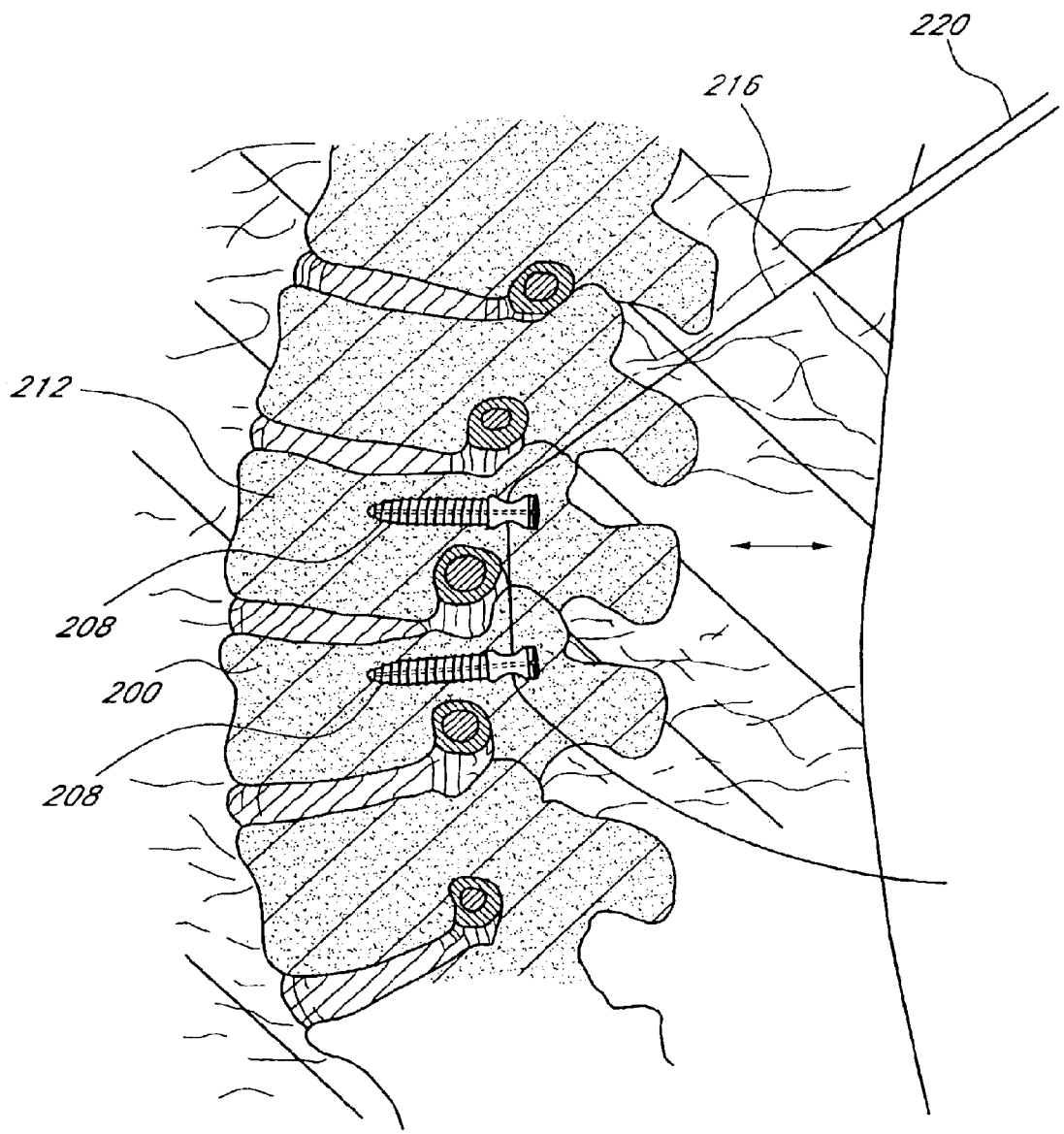

Then, as shown in FIG. 25, the entire guidewire tract is dilated using a high pressure balloon and a flexible introducer sheath 220 is passed over the guidewire 216 along the entire guidewire tract exiting the caudal-ward stab incision. The guidewire 216 is removed after the introducer sheath 220 is placed.

Figure 26:
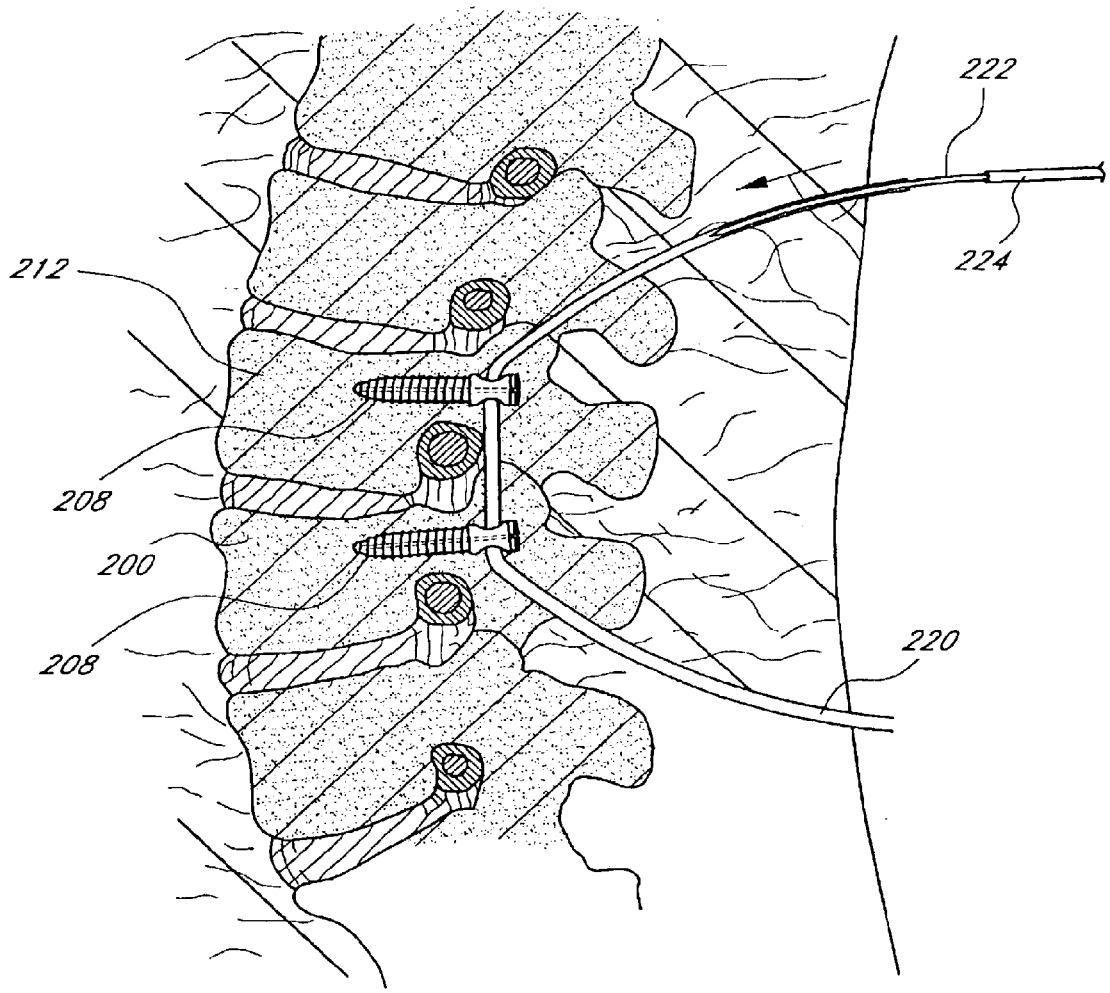

Next, as shown in FIG. 26, an uninflated, inflatable connection rod 222 according to the present invention which is attached to a proximal pushing catheter 224 is advanced through the introducer sheath 220 until the inflatable connection rod 222 advances between the two portals and the proximal end of the inflatable connection rod 222 lies cranial to the portal on the bone screw 208 in the cranial-ward vertebra 212 while the distal end of the inflatable connection rod 222 lies caudal to the portal on the bone screw 208 in the caudal-ward vertebra 200. The sheath 220 is removed and the placement is confirmed by fluoroscopy.

Figure 27:
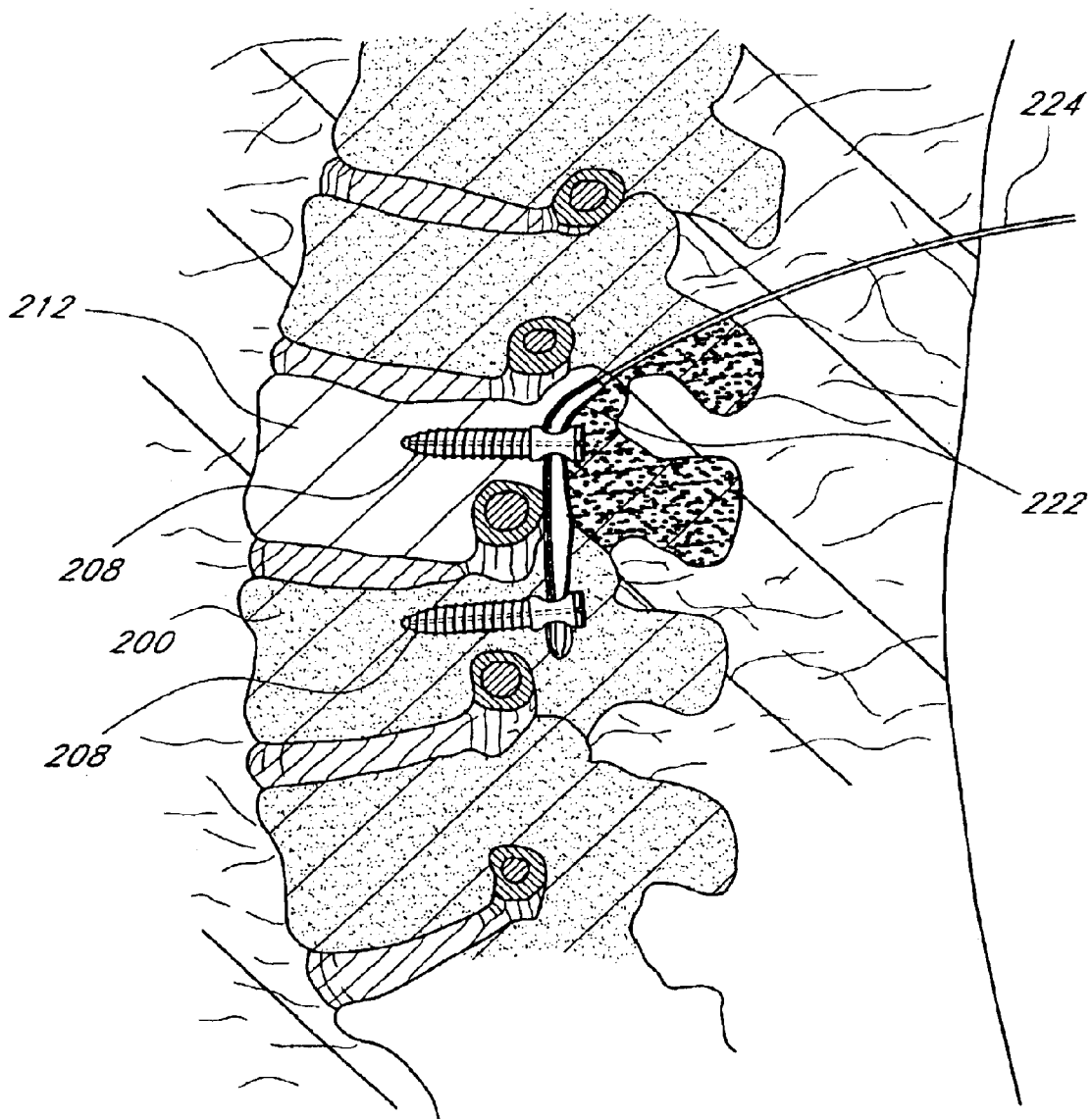

Then, as shown in FIG. 27, the balloon of the inflatable connection rod 222 is inflated with a rapid setting, liquid polymer, or its equivalent, and the polymer is allowed to set fixing each bone screw 208 in relation to each other and repositioning and fixing the vertebra 200 or portion of the vertebra that was unstable, separated or displaced. In one embodiment, the liquid polymer is or includes polymethylmethacrylate or other hardenable media such as those discussed elsewhere herein. The inflated balloon of the inflatable connection rod 222 expands radially beyond the diameter of the portals of each bone screw 208 which helps fix the bone screws 208 in relation to each other.

Figure 28:
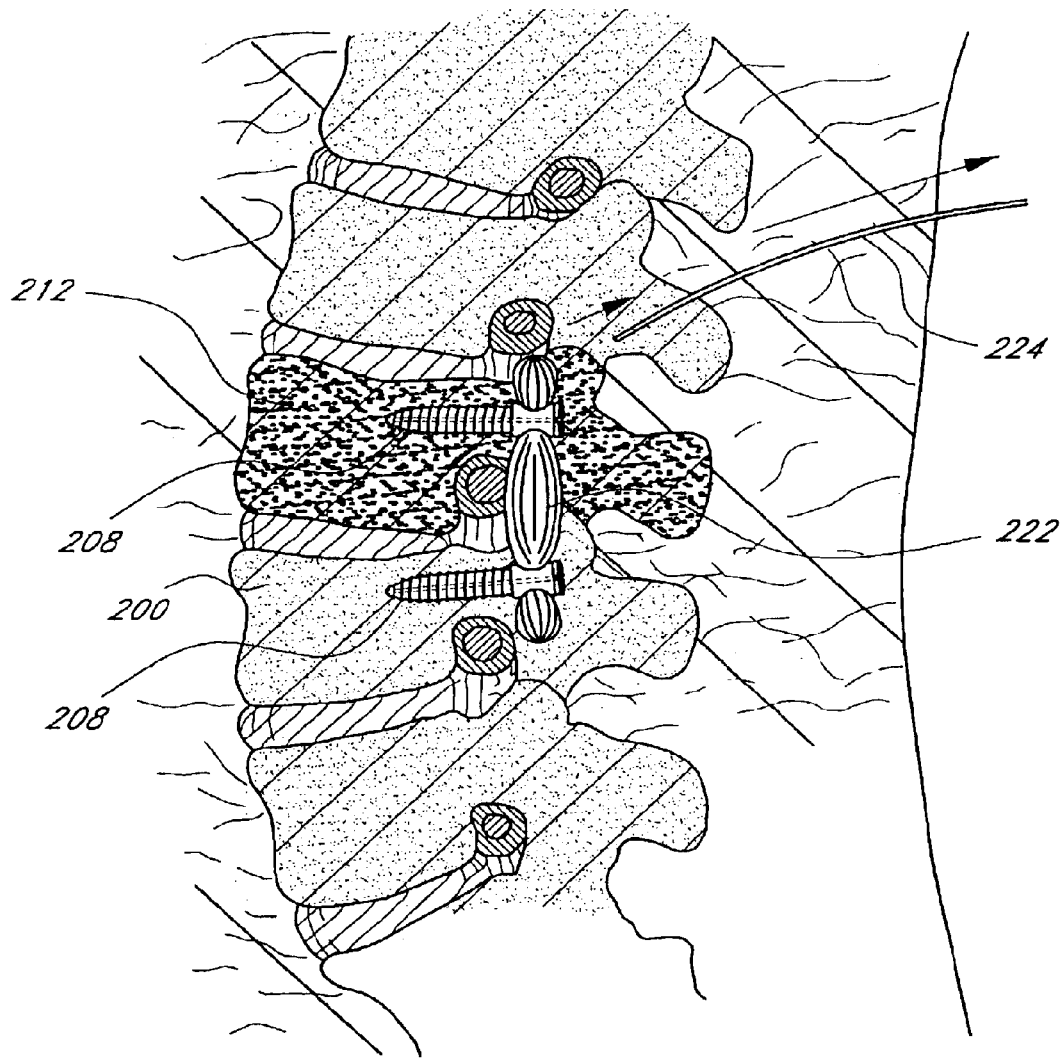

Finally, as shown in FIG. 28, the delivery or pushing catheter 224 is detached from the inflatable connection rod 222 by pulling on the pushing catheter 224 while resisting proximal movement of the inflatable connection rod 222 to disengage the inflatable connection rod 222 from the pushing catheter 224 and the pushing catheter 224 is removed. The inflatable connection rod 222 comprises a self-sealing valve which prevents the polymer from leaking once the pushing catheter is detached. The vertebra is then fixed unilaterally. The method can be repeated on the opposite side of the spinous processes of the patient's vertebrae column, thereby repositioning or fixing the one or more unstable, separated or displaced vertebrae or the one or more portions of one or more vertebrae bilaterally. The stable incisions are closed or sealed as necessary and routine postoperative care administered.

Figure 29:
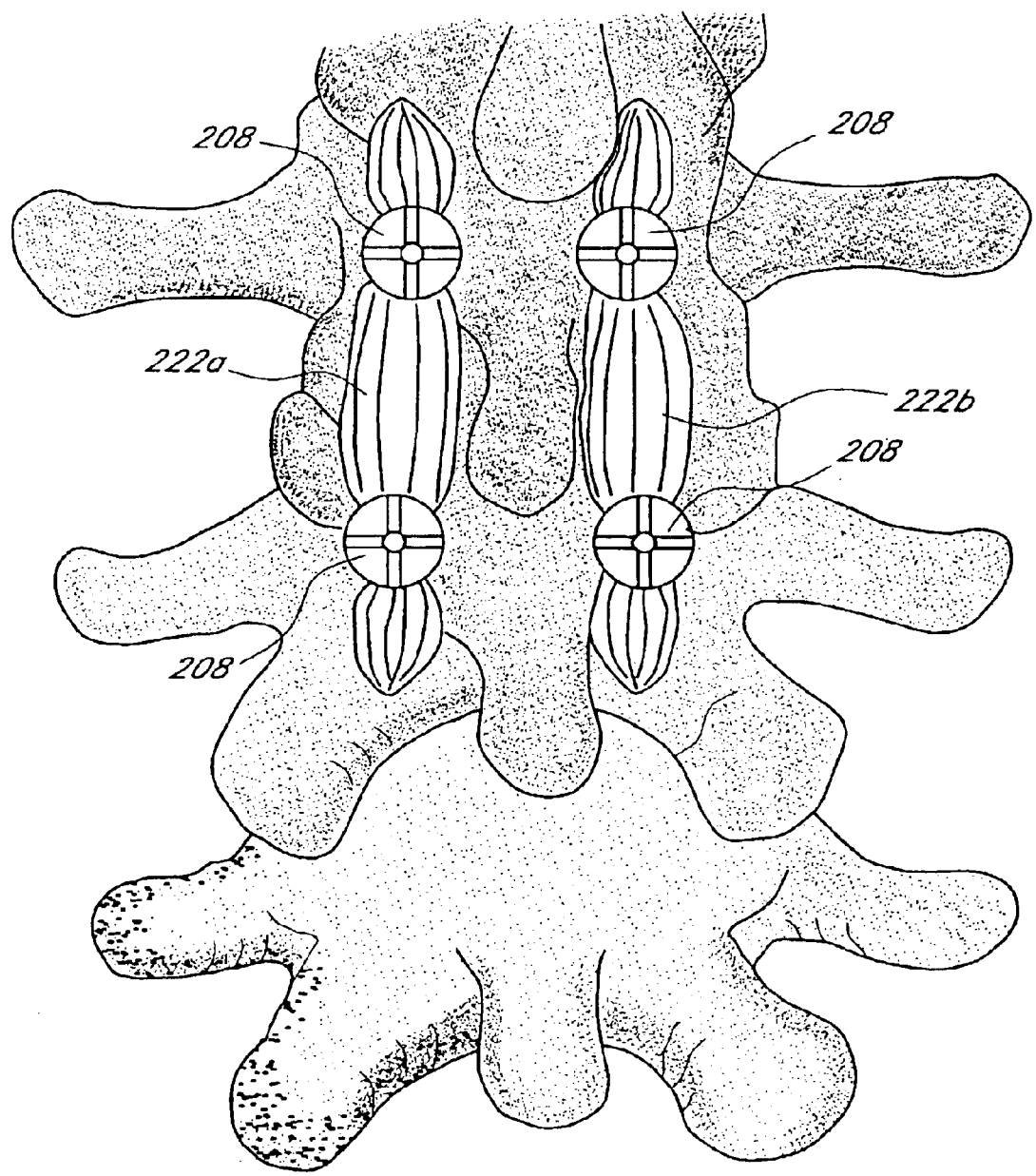
FIG. 29 is a posterior elevational view of a portion of a vertebral column post-procedure, with two fixation devices mounted thereon.

Referring now to FIG. 29, there is shown a posterior perspective view of a portion of a vertebral column which has had some vertebrae repositioned and fixed bilaterally according to the present invention. When bilateral fixation is accomplished, it is preferred to place all bone screws before connecting the portals with inflatable connection rods.

Figure 30:
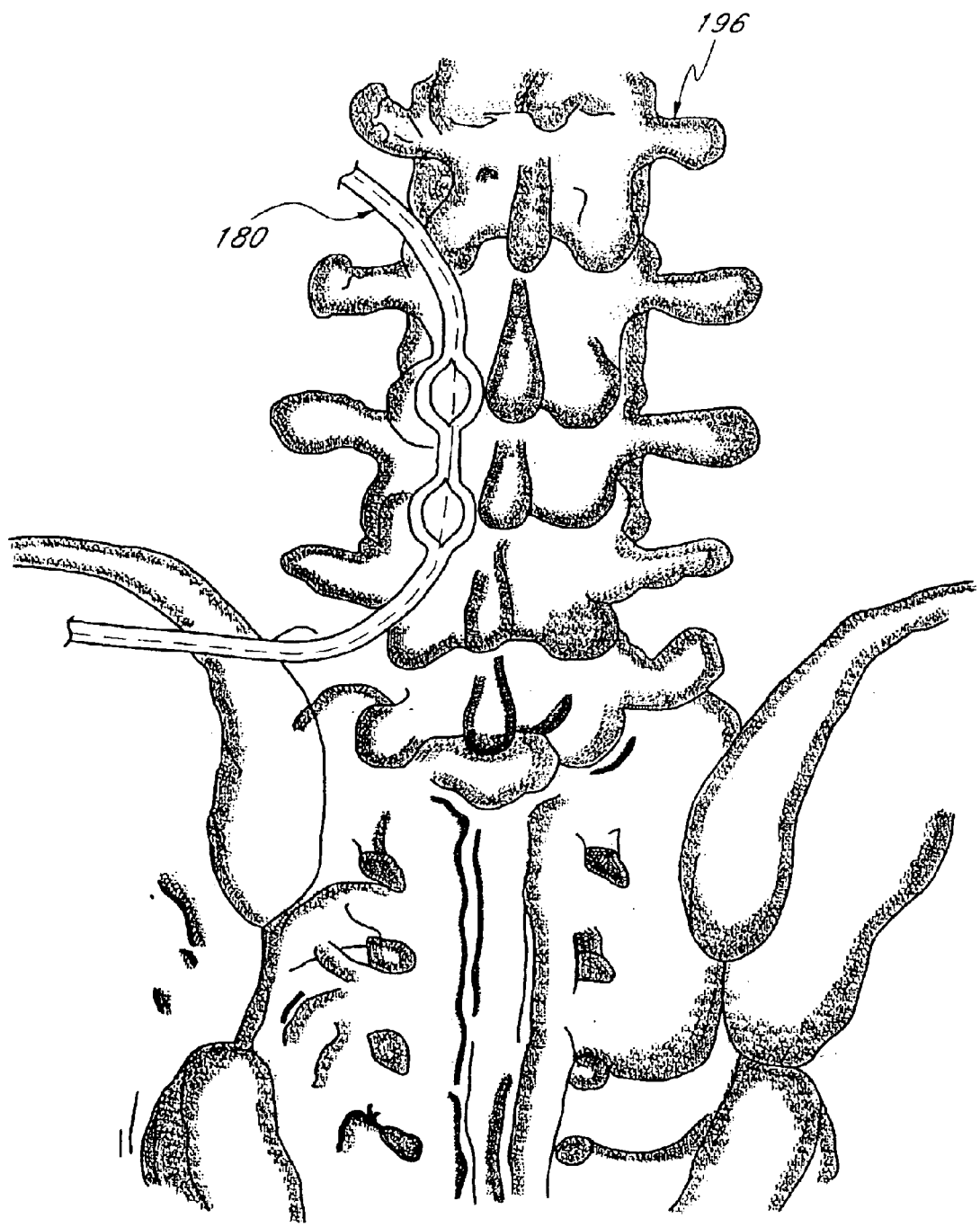
FIGS. 30–32 are posterior elevational views of a portion of a vertebral column showing a method of the present invention using a directing sheath.
Figure 31:
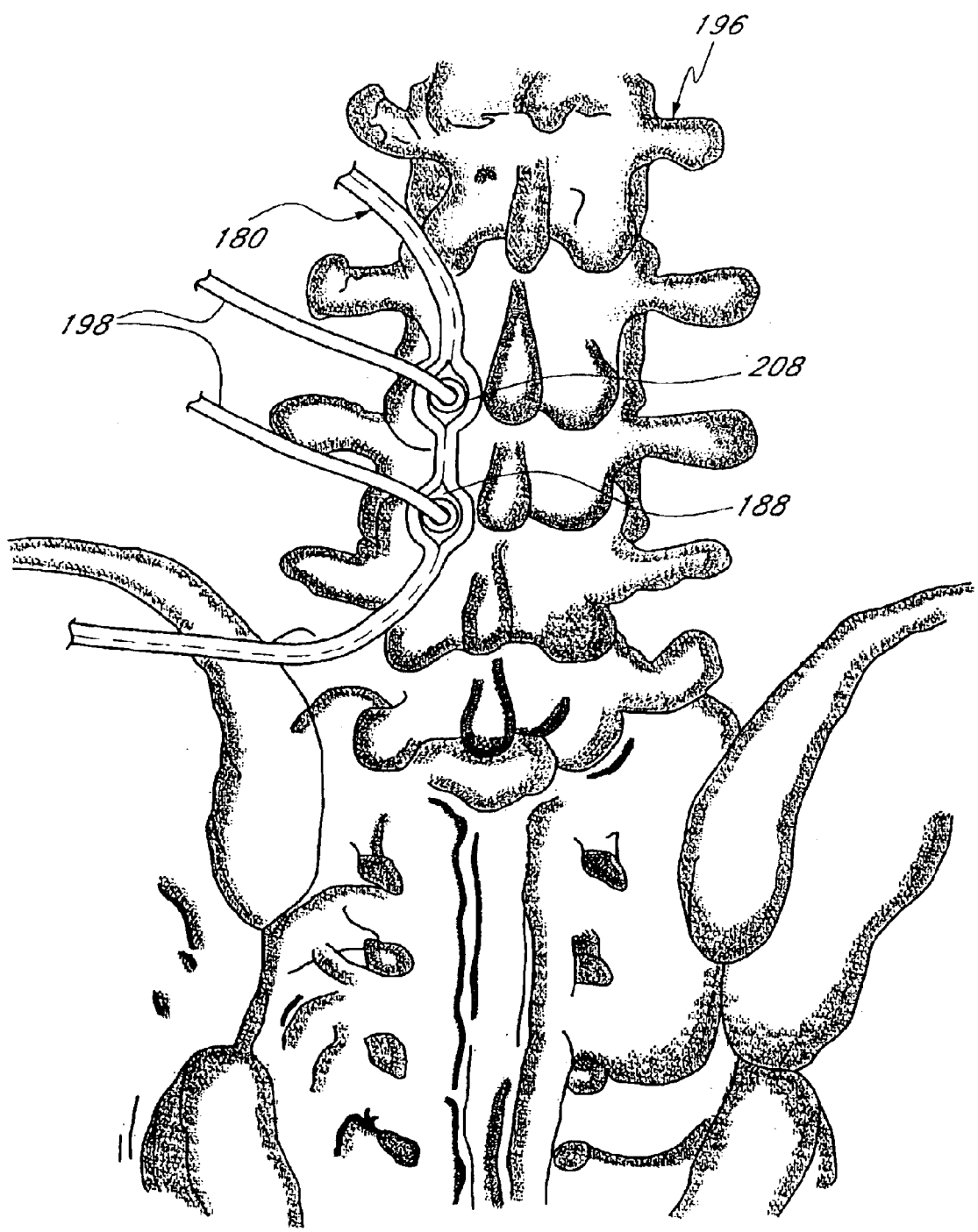
Figure 32:
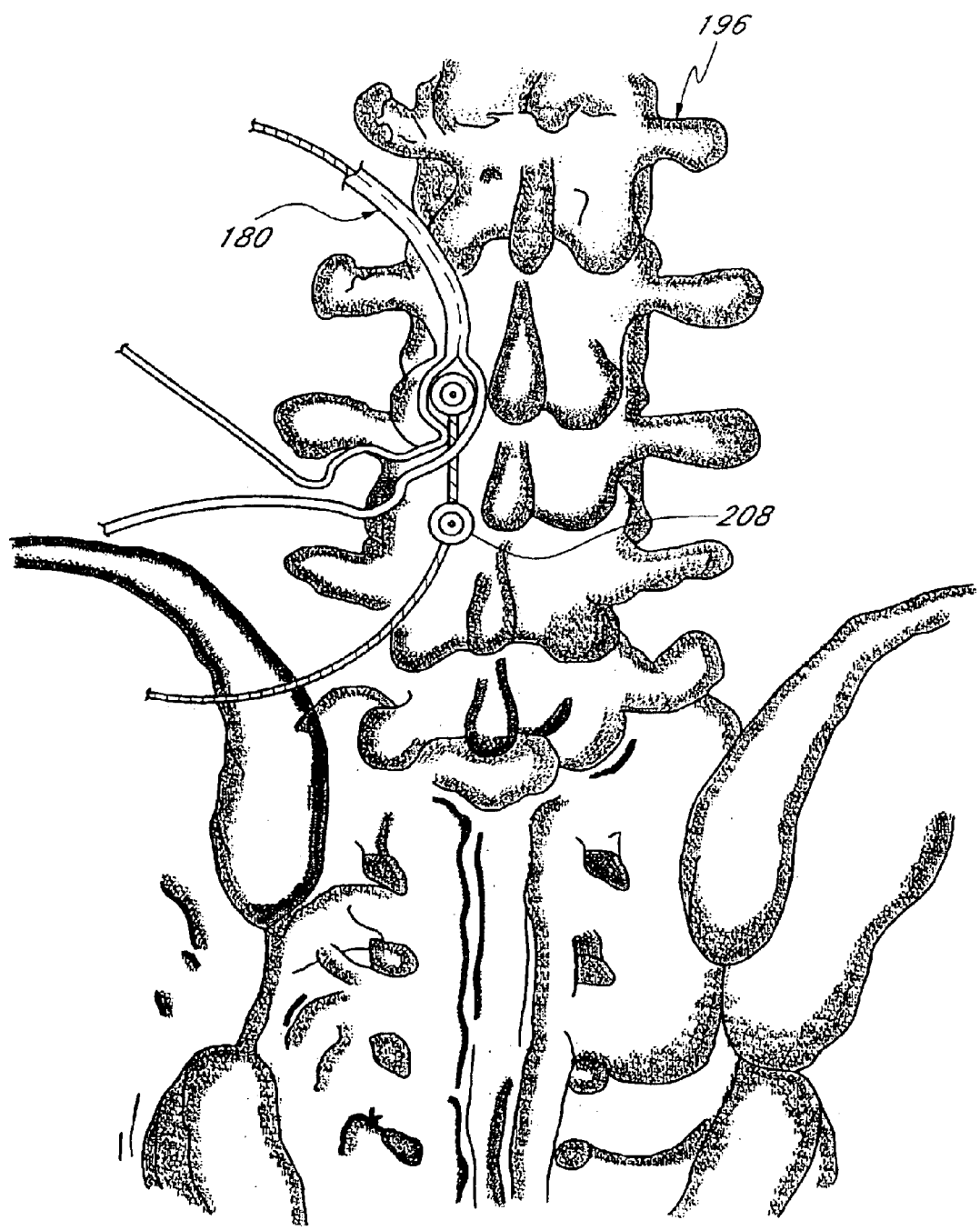

In another embodiment of the present method, a directing sheath 300 according to the present invention is advanced over a guidewire until the openings in the directing sheath 300 overlie the position in each vertebra which will receive a bone screw 208. The bone screws 208 are then placed as disclosed in this disclosure, but through the openings in the directing sheath 300, which aligns the lumen in the directing sheath with the portals of the bone screw 208. Then (not shown), a guidewire is then inserted into the lumen of the directing sheath at the proximal end of the directing sheath and advanced until the guidewire passes through each portal of the bone screws and exits the body through the lumen of the directing sheath at the distal end. The directing sheath is then removed by peeling the sheath apart along the scored lines and pulling the two halves out from the body. The guidewire that was in the lumen of the directing sheath remains in place to guide the placement of the uninflated, inflatable connection rod. Alternately, the uninflated, connection rod can be inserted directly into the lumen of the directing sheath at the proximal end and advanced until the uninflated, inflatable connection rod is properly positioned between the portals of the bone screws. Referring now to FIGS. 30 through 32, there are shown posterior perspective views of a portion of a vertebral column undergoing the method of the present invention using a directing sheath according to the present invention, showing the bone screws placed through the openings of the directing sheath. As can be seen in FIG. 30, the directing sheath 300 is positioned adjacent the vertebral column 302 according to the present invention. Next as can be seen in FIG. 31, guidewires 304 are used to place bone screws 306 through openings 308 in the directing sheath 300. Finally, as can be seem in FIG. 32, the directing sheath 300 is removed by the directing sheath 300 into two separate halves.

In one embodiment, there is provide a kit for performing the method of the present invention. The kit comprises a plurality of bone screws according to the present invention. The kit can also comprise other components of the system of the present invention, such as a guidewire directing device, an inflatable connection rod, the components of the polymer system to be mixed and injected and a directing sheath. In another preferred embodiment, the kit also comprises a screwdriver according to the present invention.

Referring to FIG. 29, a first inflatable connection rod 222a and a second inflatable connection rod 222b are illustrated as extending generally in parallel with each other, and also generally in parallel to the longitudinal axis of the spine. Deviations from this illustrated parallel relationship may also occur, in either or both of the lateral plane as well as the anterior/posterior plane. Such deviations from parallel may be a consequence of anatomical variations, or procedural choices or irregularities as will be appreciated by those of skill in the art. In any of these configurations, additional stability may be achieved by cross-linking the first inflatable connection rod 222a with the second inflatable connection rod 222b. Thus, in accordance with a further aspect of the present invention, there is provided a method and apparatus for cross-linking two or more inflatable connection rods.

Cross-linking may be accomplished in any of a variety of configurations, as will be apparent to those of skill in the art in view of the disclosure herein. For example, a pair of laterally opposing pedicle screws 208 may be connected to each other by an inflatable crossbar or solid crossbar as will be apparent from the disclosure herein. Alternatively, the body of the two opposing inflatable connection rods 222a and 222b can also be connected by a crossbar. Although the present discussion will focus primarily upon the latter construction, it is to be understood that the present invention contemplates any cross connection between a left and right connection rod, preferably through a procedure in which each of the connection rods or crossbars is installed in a less invasive or minimally invasive procedure.

Figure 33:
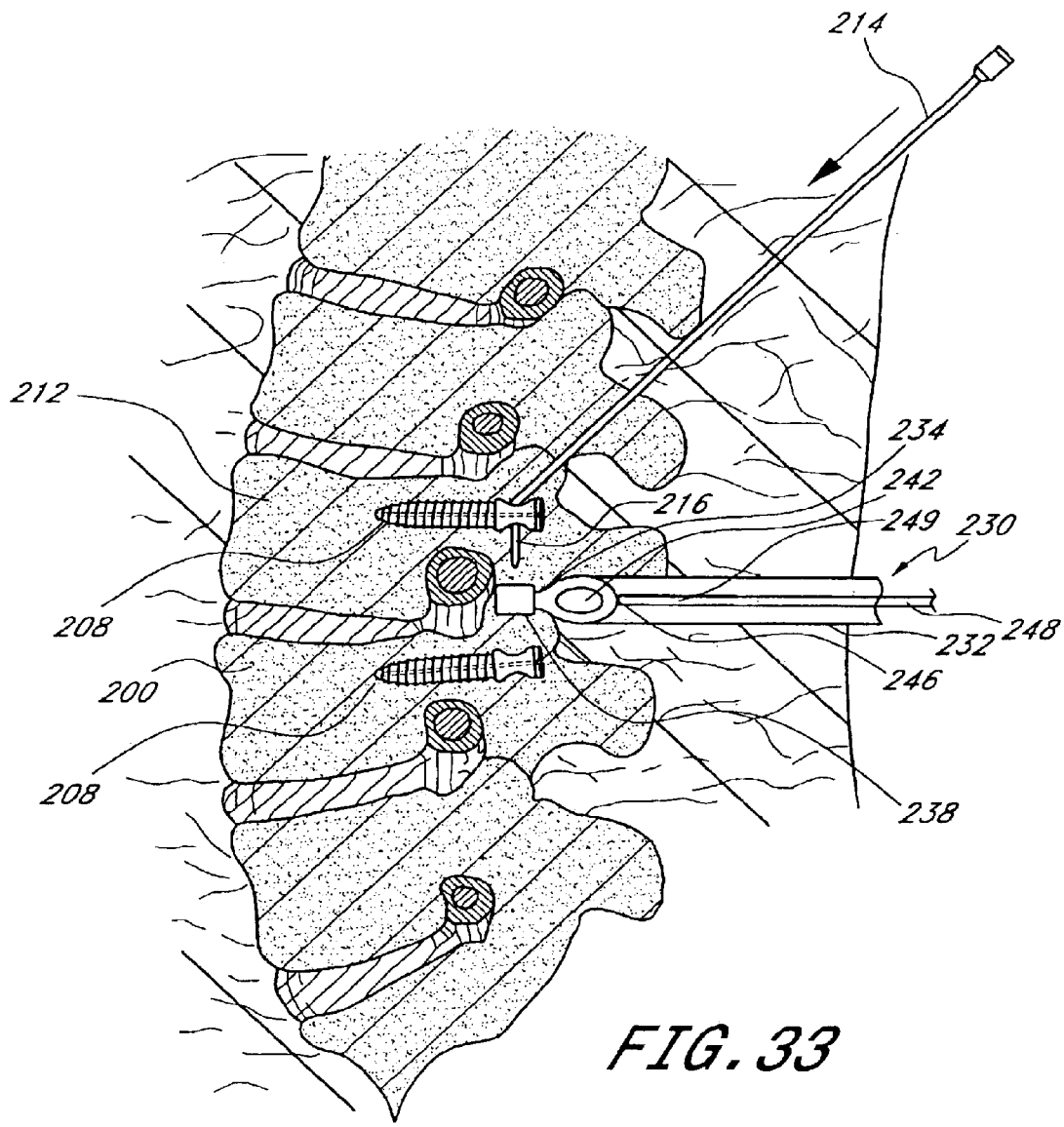
FIG. 33 is a side elevational view of a cross tie held in position by a cross tie deployment system, in-between a first and a second pedicle screw.

Referring to FIG. 33, a side elevational view of a portion of the spine is illustrated. A first and second pedicle screws 208 have been positioned in accordance with procedures discussed previously herein. A hollow needle 214 is illustrated, for guiding a "rocketwire" or guidewire 216 through the coaxial apertures in the first and second pedicle screws 208.

FIG. 33 additionally illustrates a cross tie deployment system 230, partway through a deployment procedure. The cross tie deployment system 230 comprises an access sheath 232. Access sheath 232 comprises an elongate tubular body having a proximal end and a distal end, and a central lumen extending therethrough. In general, the central lumen will have a diameter within the range of from about 24 French to about 30 French, although other diameters may be utilized depending upon the size of the device to be deployed. The access sheath 232 is positioned through tissue along an axis which intersects the path of the guidewire 216, as is advanced from a first pedicle screw 208 through an aperture in a second pedicle screw 208, as illustrated.

A cross tie support 248 is axially movably positioned within the access sheath 232. Cross tie support 248 is connected at a distal end 249 through a releasable connector 246 to a cross tie 234. Cross tie 234 facilitates connection of a crossbar with a primary inflatable connection rod, to achieve cross linking of the orthopedic fixation system.

Although a variety of structures for cross tie 234 can be utilized, one convenient construction is illustrated in FIG. 37. In general, the cross tie 234 includes a first connector 236 such as a first aperture 238 for receiving an inflatable connection rod 222 as has been discussed previously herein. In one implementation, the aperture 238 has an inside diameter of approximately 6 mm. However, diameters of the first aperture 238 may be varied widely, depending upon the diameter of the inflatable connection rod 222, and the desired physical performance characteristics.

Figure 35:
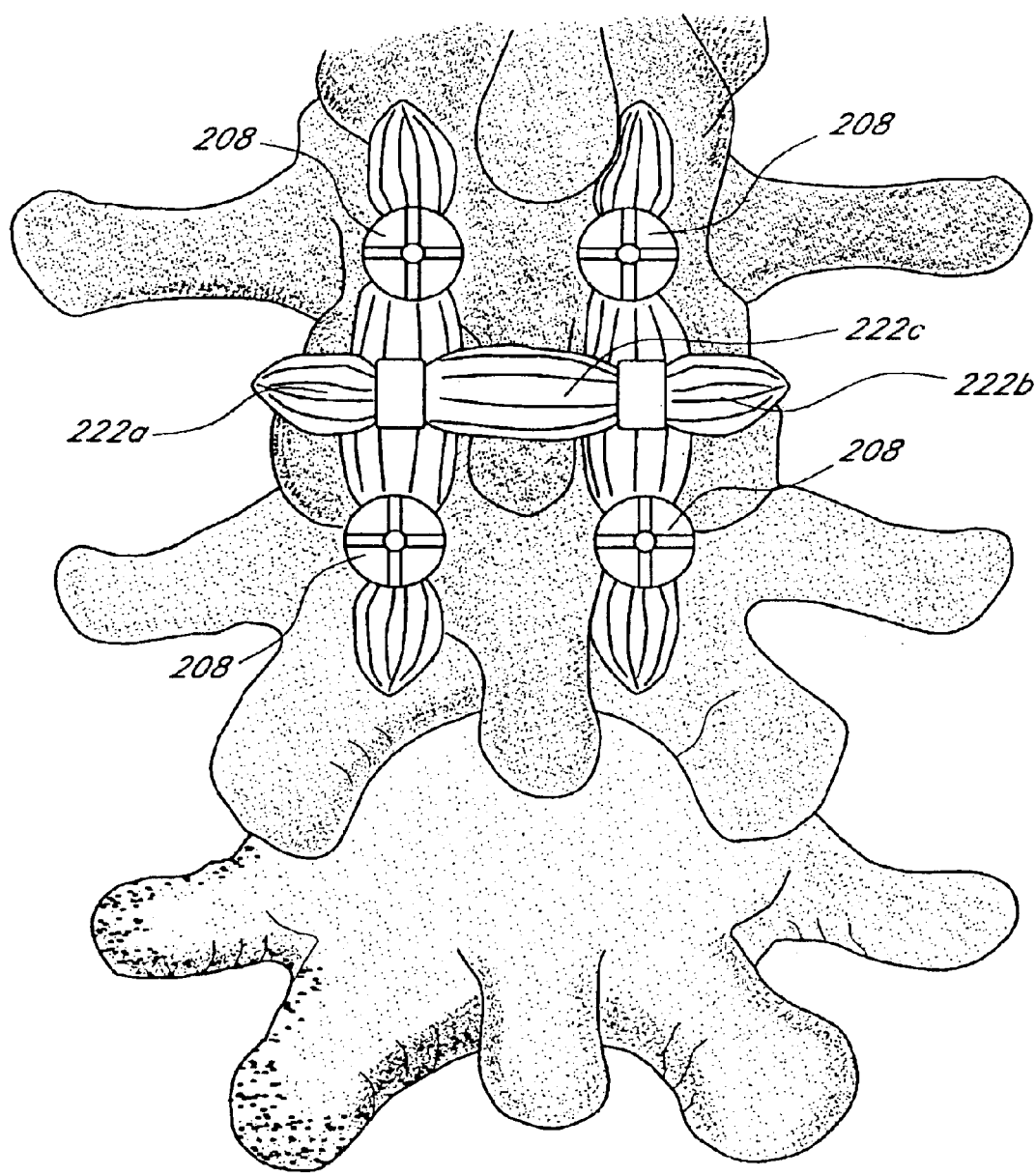
FIG. 35 is a posterior elevational view of a portion of a vertebral column, post procedure, with two inflatable connection rods and one crossbar mounted thereon.

The cross tie 234 additionally comprises a second connector 240, such as a second aperture 242. The second aperture 242 is adapted to receive a crossbar 222c, as illustrated in FIGS. 35 and 36. In the illustrated cross tie 234, a longitudinal axis extending through the first aperture 238 is generally perpendicular to a longitudinal axis extending through a second aperture 242, and offset by a spacing distance which will determine the anterior-posterior spacing between the axis of an inflatable connection rod 222a and a corresponding crossbar 222c. In one embodiment, the overall as mounted anterior-posterior length of the cross tie 234 is approximately 16 mm, and the width of the cross tie 234 is no more than about 8 mm.

The cross tie 234 is held in place during the procedure by a cross tie support 248 through a releasable connector 246. The releasable connector 246 facilitates the positioning of the cross tie 234 during the deployment step, but enables decoupling following proper positioning of at least an inflatable connection rod 222a and possibly also the crossbar 222c. Any of a variety of releasable connection structures may be utilized, such as a threaded distal end on the cross tie support 248, which threadably engages an aperture on the cross tie 234.

As illustrated in FIGS. 33, 36 and 37, the cross tie 234 is held in position by the cross tie support 248 such that the longitudinal axis extending through the first aperture 238 is colinear with the path of the guidewire 216. The longitudinal axis of the second aperture 242 extends transversely such that it aligns with a second aperture 242 in a second cross tie 234 to accomplish the cross-linked construction illustrated in FIGS. 35 and 36.

Figure 34:
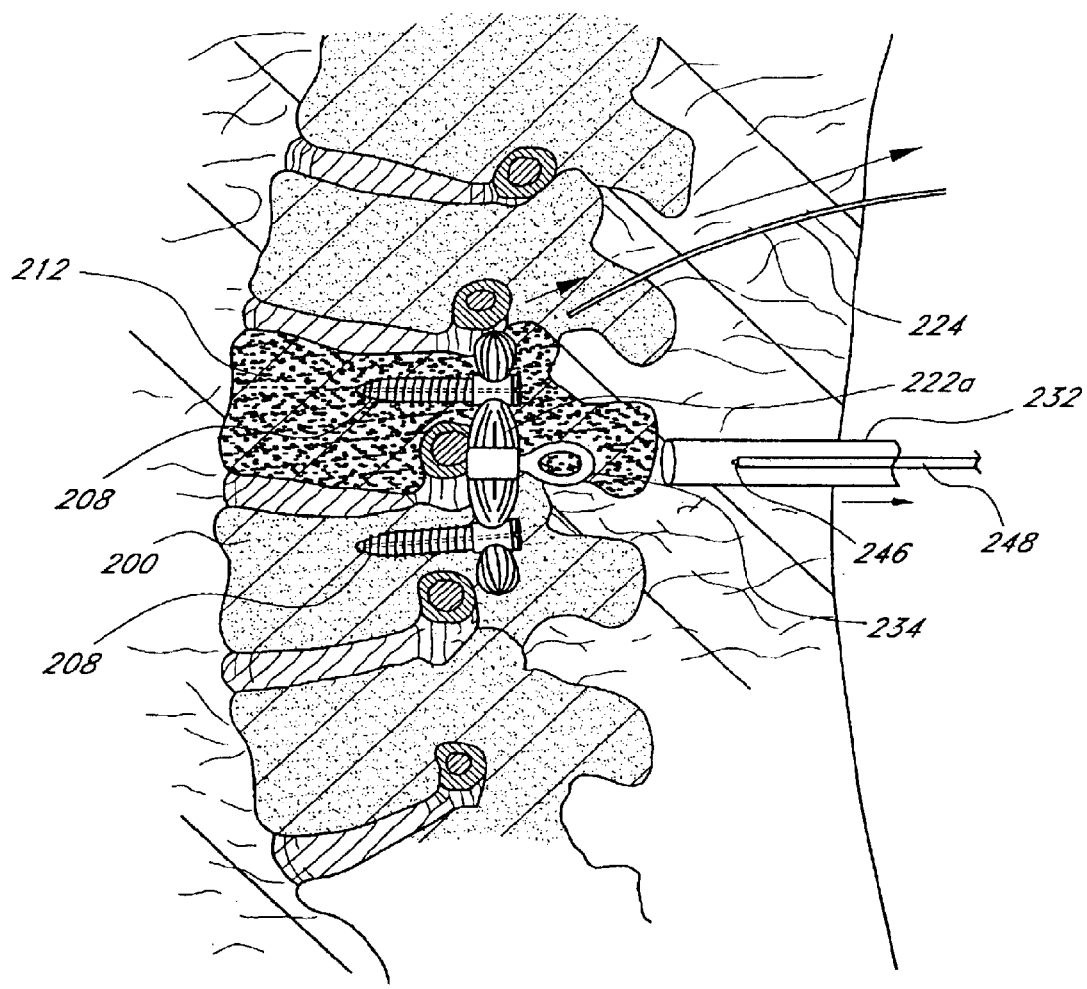
FIG. 34 is a side elevational view as in FIG. 33, illustrating an inflatable connection rod inflated between the first and second pedicle screws, with a cross tie mounted thereon.

Referring to FIG. 34, the first inflatable connection rod 222a is illustrated as inflated after having been positioned through the first aperture 238 on the cross tie 234, as well as through the approximately colinear apertures on a pair of bone screws 208. This is accomplished by advancing the guidewire 216 through the first bone screw, then the first aperture 238 and then the second bone screw 208, as illustrated in progress in FIG. 33. The connection rod 222a may then be advanced over the wire and inflated following the inflatable connection rod implantation procedures discussed previously herein.

Preferably, the first aperture 238 is dimensioned with respect to the connection rod 222a such that a secure fit is provided between the inflatable connection rod 222a and cross tie 234 following complete curing of the curable media. If shrinkage of the curable media is contemplated, the first aperture 238 may be defined within an annular ring on the frame 244 which has an expansion break extending therethrough. In this manner, inflation of the inflatable connection rod 222a can be accomplished such that the expansion break allows a slight enlargement of the diameter of the first aperture 238. Upon transverse shrinkage of the inflatable connection rod 222a during the curing process, the natural bias imparted by the frame 244 allows the first aperture 238 to shrink, thereby retaining a tight fit with the inflatable connection rod 222a throughout a range of diameters. This construction may also be applied to the apertures extending through the bone screws 208, as well as the second apertures 242.

The cross tie support 248 is illustrated in FIG. 34 as detached from the cross tie 234, such as by unscrewing the releasable connector 246. This may be accomplished before or after positioning of the crossbar 222c, depending upon the clinical judgment of the practitioner.

The final construction is illustrated in FIG. 35. As seen therein, a crossbar 222c extends between a first cross tie 234 carried by the first inflatable connection rod 222a and a second cross tie 234 carried by the second inflatable connection rod 222b. The crossbar 222c may be positioned through the pair of opposing apertures 242 using the same techniques discussed and illustrated previously herein for the implantation of the inflatable connection rods 222. The initial position of a curved needle and guidewire for positioning the crossbar 222c is schematically illustrated in FIG. 36.

Although only a single crossbar 222c is illustrated, two or three or four or more crossbars 222c may alternatively be used, depending upon the axial lengths of the inflatable connection rods 222a and 222b, and the desired structural integrity of the finished assembly. In addition, although the crossbar 222c is illustrated as extending generally perpendicular to the longitudinal axis of each of the inflatable connection rods 222a and 222b, the crossbar 222c may cross each of the inflatable connection rods 222 at any of a variety of angles ranging from approximately +45° to −45° with respect to the illustrated position. Thus, the crossbar 222c may be implanted at a diagonal if the desired structural integrity can be thus achieved.

The crossbar 222c may comprise any of a variety of forms. For example, the crossbar illustrated in FIG. 35 may be identical in construction to any of the inflatable connection rods discussed previously herein.

In an alternate application of the cross-linking technology of the present invention, the crossbar is constructed in a manner which enables elimination of the separate cross tie 234. Referring to FIGS. 40–43, the crossbar comprises a first portal 250, for receiving a first inflatable connection rod 222a, and a second portal 252 for receiving a second inflatable connection rod 222b. First portal 250 and second portal 252 are spaced apart by an elongate tubular body 254. Body 254 may be a solid element, such as a polymeric extrusion, molded part or metal rod. Alternatively, body 254 comprises a tubular sleeve, such as illustrated in FIGS. 40–42. In the illustrated embodiment, the tubular sleeve is provided with a plurality of circumferentially extending slots 254, to permit flexibility of the crossbar 222c during deployment. Slots 254 may be formed such as by laser cutting a stainless steel, nickel-titanium alloy or other tube.

FIG. 41 schematically illustrates the distal end of a deployment system 258 for deploying the crossbar 222c of FIG. 40. The tubular body 254 is carried by a dilator 260 which extends axially therethrough. In one application, the dilator 260 is approximately 21 French, for accommodating a tubular body 254 having an inside diameter of about 7 mm and an outside diameter of about 8 mm.

The 21 French dilator 260 is advanced over a stiff 0.038" guidewire, with an 8 French catheter. A 24 French pusher sheath 262 is positioned proximally of the tubular body 254.

Using this deployment system, the tubular body 254 may be positioned relative to two pairs of bone screws 208 as illustrated schematically in FIG. 42. A first pair of bone screws 208a and 208b contain apertures which coaxially align with the first portal 250. A second pair of bone screws 208c and 208d carry apertures which are coaxially aligned with a second portal 252. Once positioned as illustrated in FIG. 242, a guiding assembly such as a curved needle 214 and a rocket wire 216 may be advanced as illustrated in FIG. 42. An inflatable connection rod 222a may thereafter be advanced along the wire, and inflated to secure the first and second bone screws 208a and 208b, and also the crossbar 222c. A similar procedure may be accomplished to install a second inflatable connection rod 222b.

The tubular body 254 may by itself provide sufficient cross-linking strength for the intended purpose. Alternatively, the tubular body 254 may be filled with a curable media 266 to enhance the structural integrity of the resulting assembly. For example, as illustrated in FIG. 43, the deployment system 258 may additionally comprise an inflatable container such as an inflatable connection rod previously disclosed herein, in communication with a source of curable media through an inflation lumen. Depending upon the construction of the inflatable container, it may be filled with a hardenable media 266 either prior to or following positioning of the first inflatable connection rod 222a and second inflatable rod 222b as discussed previously herein.

Figure 38:
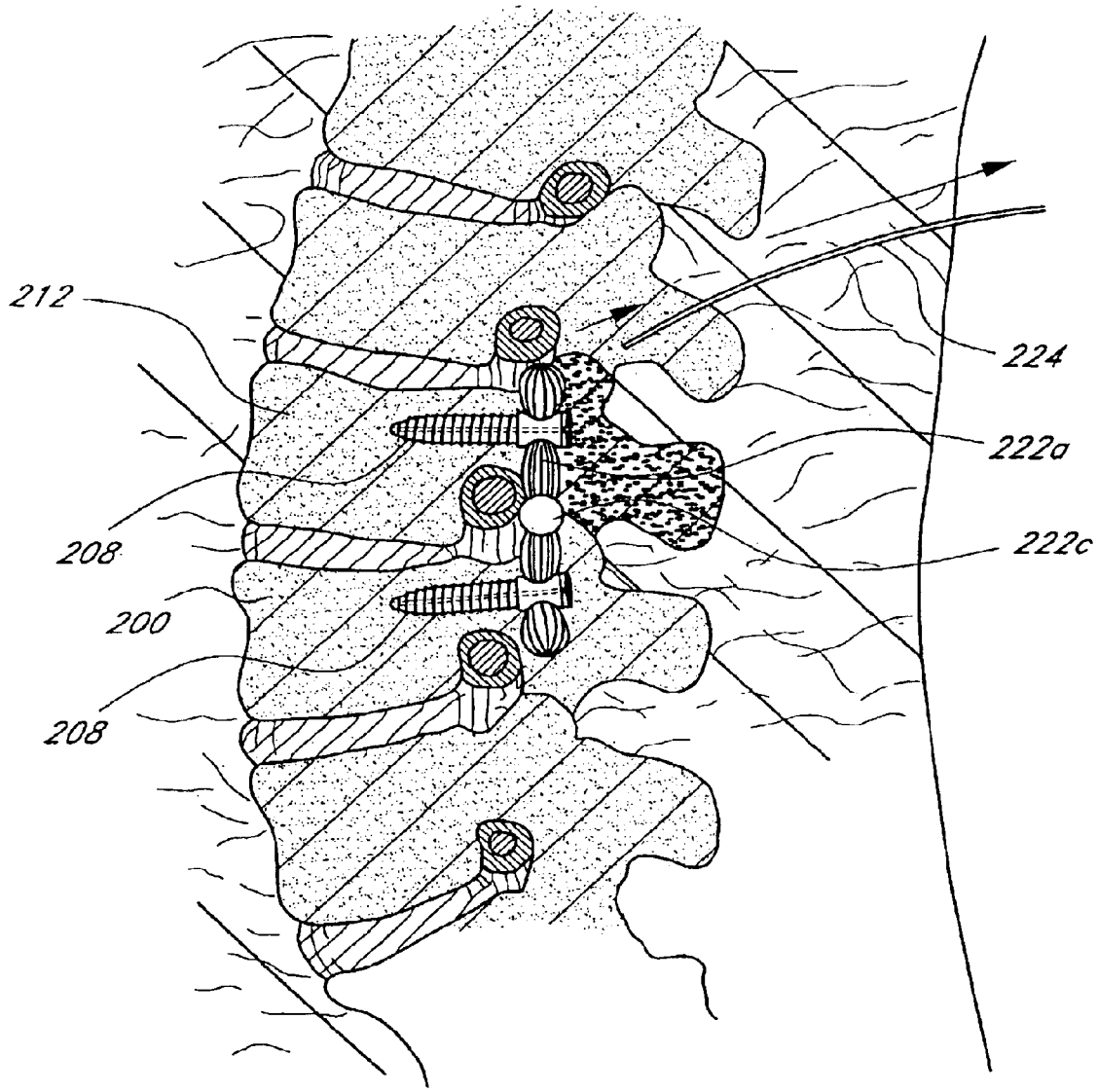
FIG. 38 is a side elevational view of a portion of a spine, having an alternate crossbar connected to an inflatable connection rod.
Figure 39:
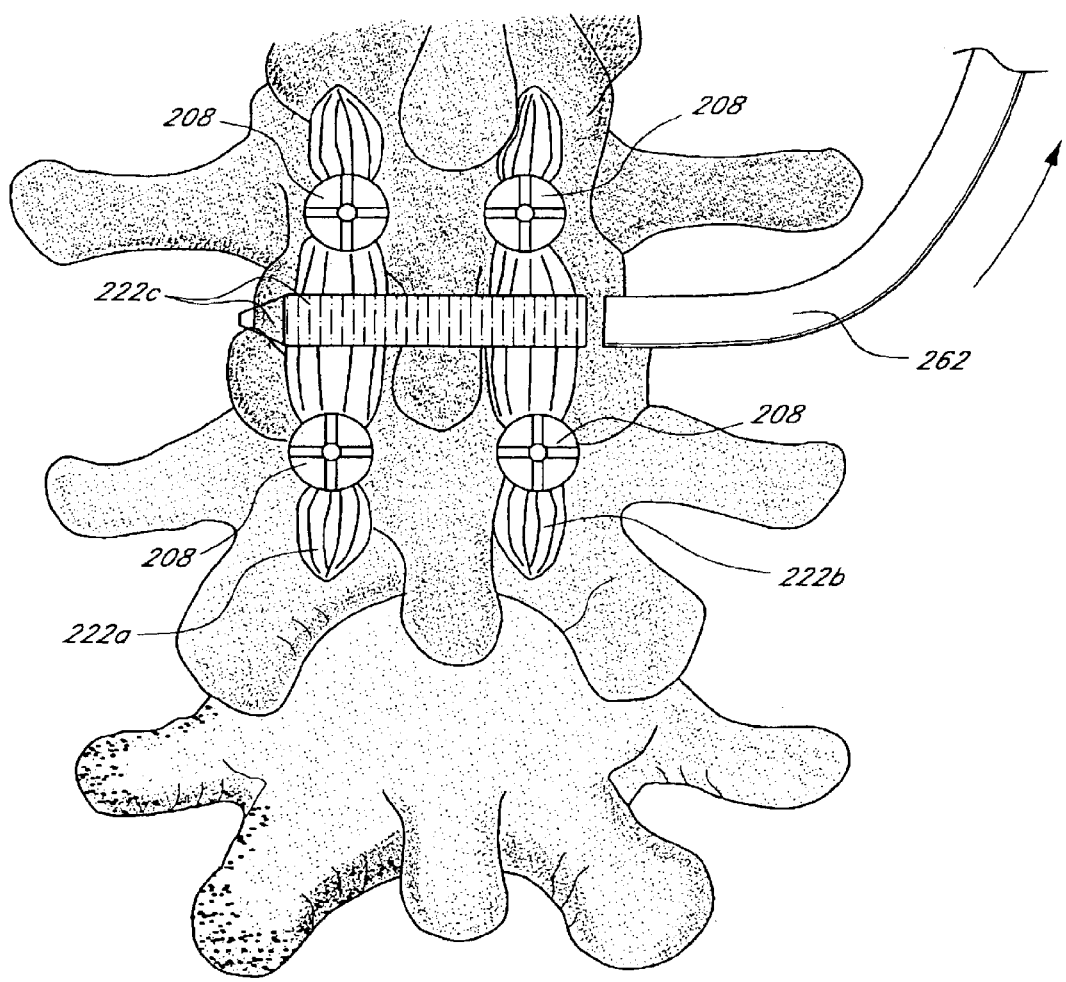
FIG. 39 is a posterior elevational view of a portion of a vertebral column, showing the crossbar of FIG. 38.

The embodiment of FIGS. 40–43 is illustrated in position within the patient, in FIGS. 38 and 39. As can be seen from FIGS. 38 and 39, the crossbar 222c resides within the plane that extends through the apertures in the bone screws 208. Thus, the crossbar 222c in the configuration illustrated in FIGS. 38 and 39 is lower profile, or positioned anteriorly of the crossbar 222c in the embodiment of FIGS. 34 and 35. The location of the crossbar 222c in FIGS. 38 and 39 is not, however, precisely to scale or in the exact or only implantable location in the spine. For example, the crossbar 222c may extend laterally through a space inbetween an adjacent pair of caudal and cephalad spinous processes. If the crossbar 222c is preferably positioned at a more caudal or cephalad position than the opening between adjacent spinous processes, or if the crossbar 222c is preferably positioned farther anteriorly than would be permitted by the transverse process or other bony structure, the crossbar 222c may extend through an aperture bored through the bone, or portions of the bone may be removed. Any of a variety of bores or drills may be utilized to bore a transverse aperture, such as through a spinous process. The crossbar 222c may thereafter be advanced through the bore and locked into place using the first and second support structure 222a and 222b as is disclosed elsewhere herein.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A subcutaneously assembled in place orthopedic construct, comprising:
   a first support structure, configured to be attached to the spine;
   a second support structure, configured to be attached to the spine; and
   a cross bar, which connects the first support structure to the second support structure to form an orthopedic construct;
   wherein the cross bar is attached to the first and second support structures subcutaneously; and
   wherein at least the first support structure comprises:
      an outer wall, defining a cavity therein;
      a plurality of reinforcing fibers in the cavity; and
      a hardenable media for bonding with the reinforcing fibers to form the support structure;
   wherein the hardenable media is hardened while the support structure is positioned within the body of a patient to create the orthopedic construct.

2. A subcutaneously assembled in place construct as in claim 1, wherein the second support structure comprises a hardenable media.

3. A subcutaneously assembled in place construct as in claim 2, wherein the cross bar comprises a hardenable media.

4. A subcutaneously assembled in place construct as in claim 1, further comprising a first cross tie connecting the cross bar to the first support, and a second cross tie connecting the cross bar to the second support.

5. A subcutaneously assembled in place construct as in claim 1, wherein the cross bar includes a first aperture for receiving the first support, and a second aperture for receiving the second support.

6. A subcutaneously assembled in place construct as in claim 1, further comprising a first bone anchor configured for connecting the first support structure to a first vertebral body, and a second bone anchor configured for connecting the first support structure to a second vertebral body.

7. A subcutaneously assembled in place construct as in claim 6, wherein the first support structure extends through an aperture in the first bone anchor.

8. A subcutaneously assembled in place construct as in claim 1, wherein the hardenable media comprises an epoxy.

9. A subcutaneously assembled in place construct as in claim 1, wherein the hardenable media comprises polyurethane.

10. A subcutaneously assembled in place construct as in claim 1, wherein the reinforcing fibers comprise carbon fibers.

11. A subcutaneously assembled in place construct as in claim 1, wherein the reinforcing fibers comprise graphite fibers having a diameter within the range of from about 0.003 inches to about 0.007 inches.

12. A subcutaneously assembled in place construct as in claim 1, wherein the reinforcing fibers are provided in at least one bundle having within the range of from about 3,000 to about 12,000 fibers.

13. A subcutaneously assembled in place construct as in claim 12, comprising from about 30 to about 60 bundles of fibers.

14. A subcutaneously assembled in place construct as in claim 1, wherein the reinforcing fibers have a Tow tensile strength within the range of from about 5,000 Mpa to about 7,000 Mpa.

15. A subcutaneously assembled in place construct as in claim 1, wherein the reinforcing fibers have a Tow tensile modulus within the range of from about 250 Gpa to about 350 Gpa.

16. A subcutaneously assembled in place construct as in claim 1, further comprising at least one reinforcing sleeve within the cavity.

17. A subcutaneously assembled in place construct as in claim 1, wherein the reinforcing sleeve comprises a braided carbon fiber wall.

18. A method of treating the spine, comprising the steps of:
   attaching a first support structure to the spine;
   attaching a second support structure to the spine; and
   introducing a curable media into at least the first support structure while it is positioned between the spine and a muscle layer
   permitting the curable media in the first support to cure within the body;
   attaching a cross bar to the first and second support structures;
   wherein at least the attaching a cross bar step comprises advancing at least a portion of the cross bar between the spine and a muscle layer.

19. A method of treating the spine as in claim 18, further comprising attaching a first bone anchor to a first vertebral body and a second bone anchor to a second vertebral body.

20. A method of treating the spine as in claim 19, further comprising connecting the first bone anchor and the second bone anchor to the first support structure.

21. A method of treating the spine as in claim 20, further comprising inserting the first support structure through an aperture in the first bone anchor.

22. A method of treating the spine as in claim 21, further comprising inserting the first support structure through an aperture in the second bone anchor.

23. A method of treating the spine as in claim 18, further comprising inserting the first support through a first aperture in the cross bar.

24. A method of treating the spine as in claim 23, further comprising inserting the second support through a second aperture in the cross bar.

25. A subcutaneously assembled in place orthopedic construct, comprising:
   a first support structure, configured to be attached to the spine;
   a second support structure, configured to be attached to the spine; and
   a cross bar, which connects the first support structure to the second support structure to form an orthopedic construct;
   wherein the cross bar is attached to the first and second support structures subcutaneously; and
   wherein at least the first support structure comprises a media that is hardenable while the support structure is positioned within the body of a patient.

26. A subcutaneously assembled in place construct as in claim 25, wherein the second support structure comprises a hardenable media.

27. A subcutaneously assembled in place construct as in claim 26, wherein the cross bar comprises a hardenable media.

28. A subcutaneously assembled in place construct as in claim 25, further comprising a first cross tie connecting the cross bar to the first support, and a second cross tie connecting the cross bar to the second support.

29. A subcutaneously assembled in place construct as in claim 25, wherein the cross bar includes a first aperture for receiving the first support, and a second aperture for receiving the second support.

30. A subcutaneously assembled in place construct as in claim 25, further comprising a first bone anchor configured for connecting the first support structure to a first vertebral body, and a second bone anchor configured for connecting the first support structure to a second vertebral body.

31. A subcutaneously assembled in place construct as in claim 30, wherein the first support structure extends through an aperture in the first bone anchor.

32. A subcutaneously assembled in place construct as in claim 25, wherein the hardenable media comprises an epoxy.

33. A subcutaneously assembled in place construct as in claim 25, wherein the hardenable media comprises polyurethane.

* * * * *